US007776604B2

(12) United States Patent
Brown et al.

(10) Patent No.: US 7,776,604 B2
(45) Date of Patent: *Aug. 17, 2010

(54) METHODS OF SELECTING AND DEVELOPING A PARTICULATE MATERIAL

(75) Inventors: Steven E. Brown, Tyngsboro, MA (US); Steven R. Reznek, Concord, MA (US); Ian D. Morrison, Acton, MA (US)

(73) Assignee: Cabot Corporation, Boston, MA (US)

( * ) Notice: Subject to any disclaimer, the term of this patent is extended or adjusted under 35 U.S.C. 154(b) by 1204 days.

This patent is subject to a terminal disclaimer.

(21) Appl. No.: 10/673,093

(22) Filed: Sep. 26, 2003

(65) Prior Publication Data

US 2004/0198887 A1 Oct. 7, 2004

Related U.S. Application Data

(60) Provisional application No. 60/491,632, filed on Jul. 31, 2003, provisional application No. 60/485,965, filed on Jul. 10, 2003, provisional application No. 60/485,964, filed on Jul. 10, 2003, provisional application No. 60/459,230, filed on Apr. 1, 2003, provisional application No. 60/497,592, filed on Aug. 25, 2003.

(51) Int. Cl.
*G01N 31/00* (2006.01)
(52) U.S. Cl. .......................... 436/2; 436/145; 73/53.01
(58) Field of Classification Search .................... 436/2, 436/145; 73/53.01
See application file for complete search history.

(56) References Cited

U.S. PATENT DOCUMENTS

| | | | |
|---|---|---|---|
| 3,229,507 A | 1/1966 | Sljaka et al. ................... 73/59 |
| 3,659,896 A | 5/1972 | Smith et al. ................... 296/93 |
| 3,950,290 A * | 4/1976 | Drury et al. ................... 524/276 |
| 4,071,496 A | 1/1978 | Kraus et al. ................... 260/42.36 |
| 4,088,628 A | 5/1978 | Bernstein et al. ................... 260/42.46 |
| 4,093,421 A | 6/1978 | Jerkins ................... 23/259.5 |
| 4,255,296 A | 3/1981 | Ogawa et al. ................... 260/5 |
| 4,259,218 A | 3/1981 | Haws ................... 260/5 |
| 4,360,627 A | 11/1982 | Okado et al. ................... 524/496 |
| 4,478,973 A | 10/1984 | Misono et al. ................... 524/496 |
| 4,540,560 A | 9/1985 | Henderson et al. ................... 423/445 |
| 4,548,980 A | 10/1985 | Nagata et al. ................... 524/495 |
| 4,678,830 A | 7/1987 | Sato et al. ................... 524/495 |
| 4,690,965 A | 9/1987 | Hirata et al. ................... 524/236 |
| 4,721,740 A | 1/1988 | Takeshita et al. ................... 523/215 |
| 4,878,379 A | 11/1989 | Deer ................... 73/60 |
| 4,914,147 A | 4/1990 | Mouri et al. ................... 524/495 |
| 4,992,190 A | 2/1991 | Shtarkman ................... 252/62.52 |
| 5,093,407 A | 3/1992 | Komai et al. ................... 524/495 |
| 5,124,396 A | 6/1992 | Branan, Jr. et al. ................... 524/496 |
| 5,128,395 A | 7/1992 | Terakawa et al. ................... 524/274 |
| 5,162,421 A | 11/1992 | Ue et al. ................... 524/495 |
| 5,190,739 A | 3/1993 | MacKay et al. ................... 423/450 |
| 5,194,488 A | 3/1993 | Piestert et al. ................... 524/703 |
| 5,211,932 A | 5/1993 | Blaylock et al. ................... 423/450 |
| 5,231,129 A | 7/1993 | Misono ................... 524/496 |
| 5,232,974 A | 8/1993 | Branan, Jr. et al. ................... 524/495 |
| 5,288,788 A | 2/1994 | Shieh et al. ................... 524/495 |
| 5,292,790 A | 3/1994 | Shimizu et al. ................... 524/496 |
| 5,303,578 A | 4/1994 | Williams et al. ................... 73/54.24 |
| 5,310,777 A | 5/1994 | Sekido et al. ................... 524/496 |
| 5,321,072 A | 6/1994 | Misono ................... 524/496 |
| 5,322,724 A | 6/1994 | Levens ................... 428/57 |
| 5,322,874 A | 6/1994 | Fujii et al. ................... 524/227 |
| 5,352,289 A | 10/1994 | Weaver et al. ................... 106/476 |
| 5,362,794 A | 11/1994 | Inui et al. ................... 624/496 |
| 5,382,621 A | 1/1995 | Laube ................... 524/496 |
| 5,405,623 A | 4/1995 | Barkalow et al. ................... 426/5 |
| 5,426,148 A | 6/1995 | Tucker ................... 524/496 |
| 5,428,099 A | 6/1995 | Morrar et al. ................... 524/495 |
| 5,430,087 A | 7/1995 | Carlson et al. ................... 524/496 |
| 5,480,626 A | 1/1996 | Klasen et al. ................... 423/449.1 |
| 5,534,578 A | 7/1996 | Wideman et al. ................... 524/396 |
| 5,547,609 A | 8/1996 | Fujii et al. ................... 252/511 |
| 5,639,817 A | 6/1997 | Probst et al. ................... 524/496 |
| 5,643,991 A | 7/1997 | Stipe et al. ................... 524/496 |
| 5,652,298 A | 7/1997 | Murray ................... 524/571 |
| 5,688,317 A | 11/1997 | MacKay et al. ................... 106/476 |
| 5,696,197 A | 12/1997 | Smith et al. ................... 524/495 |
| 5,705,555 A | 1/1998 | Guilfoy et al. ................... 524/495 |

(Continued)

FOREIGN PATENT DOCUMENTS

| | | |
|---|---|---|
| EP | 0253290 | 1/1988 |
| EP | 0453625 | 10/1991 |
| EP | 0919801 | 6/1999 |
| GB | 2378716 | 2/2003 |

OTHER PUBLICATIONS

International Search Report and Written Opinion for PCT/US2004/010261 dated Oct. 19, 2004.
International Search Report and Written Opinion for PCT/US2004/010267 dated Oct. 15, 2004.
International Search Report and Written Opinion for PCT/US2004/010259 dated Oct. 21, 2004.
Attachment A—Development History.

(Continued)

*Primary Examiner*—Lyle A Alexander

(57) ABSTRACT

The present invention relates to a method of selecting and/or developing particulate material for a composition comprising the particulate material and a matrix by using at least one homogeneous interaction parameter alone or in combination with at least one heterogeneous interaction parameter. These parameters may comprise at least one interfacial potential property value, at least one value derived from an interfacial potential property value, at least one component of an interfacial potential property value, or combinations thereof for a particulate material and for the matrix. Process and performance maps, as well as methods for mapping, are also disclosed.

35 Claims, 6 Drawing Sheets

U.S. PATENT DOCUMENTS

| | | | |
|---|---|---|---|
| 5,714,096 A | 2/1998 | Dorfman | 252/511 |
| 5,723,531 A | 3/1998 | Visel et al. | 524/496 |
| 5,733,480 A | 3/1998 | Lee et al. | 252/511 |
| 5,792,941 A | 8/1998 | Rye et al. | 73/53.01 |
| 5,801,209 A | 9/1998 | Chung et al. | 521/99 |
| 5,859,120 A | 1/1999 | Karl et al. | 524/495 |
| 5,877,250 A | 3/1999 | Sant | 524/496 |
| 5,877,251 A | 3/1999 | Sant | 524/496 |
| 5,974,167 A | 10/1999 | Reszler | 382/141 |
| 6,013,737 A | 1/2000 | Takagishi et al. | 525/332.7 |
| 6,046,266 A | 4/2000 | Sandstrom et al. | 524/492 |
| 6,056,933 A | 5/2000 | Vogler et al. | 423/449.1 |
| 6,084,015 A | 7/2000 | Chino et al. | 524/189 |
| 6,086,792 A | 7/2000 | Reid et al. | 252/511 |
| 6,096,833 A | 8/2000 | Araki et al. | 525/342 |
| 6,099,818 A | 8/2000 | Freund et al. | 423/449.1 |
| 6,156,837 A | 12/2000 | Branan, Jr. et al. | 524/495 |
| 6,197,277 B1 | 3/2001 | Fukuda et al. | |
| 6,228,928 B1 | 5/2001 | Soeda et al. | 524/495 |
| 6,277,350 B1 | 8/2001 | Gerspacher | 423/449.1 |
| 6,391,274 B1 | 5/2002 | Vogler et al. | 423/275 |
| 6,410,630 B1 | 6/2002 | Hoover et al. | 524/365 |
| 6,448,309 B2 | 9/2002 | Mahmud et al. | 523/215 |
| 6,482,883 B1* | 11/2002 | Cuch et al. | 524/492 |
| 7,021,213 B2* | 4/2006 | Sampei | 101/483 |
| 2001/0036995 A1 | 11/2001 | Mahmud et al. | 524/495 |
| 2002/0077409 A1 | 6/2002 | Sakaki et al. | 524/496 |
| 2002/0107318 A1 | 8/2002 | Yamada et al. | 524/495 |
| 2002/0156177 A1 | 10/2002 | Freund | 524/496 |
| 2002/0173582 A1 | 11/2002 | Schmidt | 524/504 |
| 2003/0097871 A1 | 5/2003 | Mansky | 73/64.49 |
| 2003/0162876 A1 | 8/2003 | Vanier et al. | 524/437 |
| 2003/0164027 A1 | 9/2003 | Terrom | 73/64.48 |

OTHER PUBLICATIONS

Strom, "Wetting studies related to offset printing," vol. 50-04C, pp. 768 (1988) Abstract only.
Tikhonov, "On the evaluation of the work of adhesion, cohesion, and surface tension of high—viscous and solid bodies," Kolloidn Zh, vol. 53, No. 3, pp. 552-558 (1991) Abstract only.
Janczuk, et al., "Surface free energy components and adsorption properties of some porous glasses," Mater Chem Phys. vol. 25, No. 2, pp. 185-198 (1990) Abstract only.
Janczuk, et al., "Surface free energy of celestite and its flotation activity," Colloids Surf. vol. 35, No. 1, pp. 41-48 (1989) Abstract only.
Wojcik et al., "Gas-adsorption studies on correlations between the flotability of minerals and the work of water adhesion to their surfaces," Colloids Surf. vol. 30, No. 3-4, pp. 275-285 (1988) Abstract only.
Lipatov, "Adhesion at the polymer mixtures-solid interface," Vide, Couches Minces, vol. 50 (274), pp. 415-420 (1994) Abstract only.
Hill, "Wall slip in polymer melts: A pseudo-chemical model," J. Rheol. vol. 42, No. 3, pp. 581-601 (1998) Abstract only.
Scheie, "The upward force on liquid in a capillary tube," Am. J. Phys. vol. 57, No. 3, pp. 278-289 (1989) Abstract only.
Lee et al., "Effects of polymer-filler interaction on the mechanical properties of nylon 6,6 filled with organosilane-treated fillers," J. Adhes. Sci. Technol., vol. 3, No. 4, pp. 291-303 (1989) Abstract only.
Abramzon et al., "Determination of the work of adhesion and cohesion" ZH. Prikladnoi Khim, vol. 53, No. 5, pp. 1040-1043 (1980) Abstract only.
Mangipudi et al., Direct measurement of molecular level adhesion between poly(ethylene terephthalate) and polyethylene films: Determination of surface and interfacial energies, J. Adhesion Sci. Technol., vol. 8, No. 11, pp. 1251-1270 (1994) Abstract only.
Owen, "Surface properties of silicone release coatings," Proc. First Internat. Congress on Adhesion Science and Technology, pp. 255-263 (1995) Abstract only.
Kaya, The effect of pore fluid contamination on a selected physico-chemical parameters of fine grained soils (Adsorption, Conductivity), vol. 57-05B, p. 3354 (1996) Abstract only.
Qin, Adhesion properties of polymeric materials (Asphalts, Cohesion), vol. 57-02B, p. 1260 (1995) Abstract only.
Stepanov, "Electrocapillary behaviour of liquid bismuth in binary melts of strontium chloride with sodium and cesium chlorides," Ehlektrokhimiya, vol. 30, No. 8, pp. 1032-1038 (1994) Abstract only.
Kulawik, et al., "Kinetics of the molecular interactions in some extraction system," ISEC '88 International solvent extraction Conference, vol. 2, pp. 77-78 (1988) Abstract only.
Nardin et al., "Stress transfer analysis in fibre/elastomer interfaces," Comptes-Rendus des Huitiemes Journess Nationales sur les Composites, pp. 289-300 (1992) Abstract only.
Maugis, "Adherence and Fracture Mechanics," Adhesive Bonding, pp. 303-335 (1991) Abstract only.
Wan et al., "Surface forces at crack interfaces in mica in the presence of capillary condensation," Acta Metallurgia et Materialia, vol. 38, No. 11, pp. 2073-2083 (1990) Abstract only.
Savenko et al., "Effect of diamond-like carbon coatings on the mechanical properties of subsurface layers of single crystals of silicon," Physics and Chemistry of Materials Treatment, vol. 31, No. 2, pp. 149-153 (1997) Abstract only.
Lellig et al., "Glass and polymer: wetting and adhesion," Glass Science and Technology, vol. 69, No. 11, pp. 357-367 (1996) Abstract only.
Maugis, "Adherence of elastomers: fracture mechanics aspects," Journal of Adhesion, vol. 23, No. 1, pp. 61-66 (1987) Abstract only.
Riande et al., "Fundamental aspects of the adhesion of polymers," Revista de Plasticos Modernos, vol. 80, No. 530, pp. 170-179 (2000) Abstract only.
Gilbert, "Surface treatments for particulate fillers in plastics," Plastics Additivies. AN A-Z reference, pp. 590-603 (1998) Abstract only.
Maltese, "Interfacial energy between polymers," Materie Plastiche ed Elastomeri, VBol. 64, Nos. ½, pp. 74-78 (1999) Abstract only.
Cherry et al., "Predicting work of adhesion using molecular modeling," Adhesion '96, Conference Proced., vol. 1, pp. 299-304 (1996) Abstract only.
Feinerman et al., "Rule of interfacial equilibrium," J. Adhesion, vol. 60, Nos. 1-4, pp. 99-112, (1997) Abstract only.
Geraghty et al., "Investigation of parameters influencing bioadhesive properties of myverol 18-99/water gels," Biomaterials, vol. 18, No. 1, pp. 63-67 (1997) Abstract only.
Wimolkiatisak et al., Directly paintable, high adhesion polyolefin compounds, Plast 21 No. 43, pp. 44-47 (1995) Abstract only.
Drzal, et al., "Adhesion of carbon fibres to polycarbonate matrices: interphase composition and structure," Antec '95. vol. 11, Conference Proceedings, pp. 2877-2881 (1995) Abstract only.
Moore, "Wetting in rubber-to-metal bonding agents," Rubb. Plast. News, vol. 24, No. 7, pp. 17-18 (1994) Abstract only.
Mangipudi et al., "Adhesion of thin polymer films: Effects of surface and interfacial energies and rheological properties," Antec '93 Conference Proceedings, vol. III, pp. 3099-3100, (1993) Abstract only.
Bautista et al., "Surface characterization of polypropylene used as a matrix in composite materials," Rev. Plast. Mod. vol. 66, No. 449, pp. 505-509 (1993) Abstract only.
Pritykin et al., "New thermodynamic characteristics of polymer adhesive properties," International Adhesion Conference, p. 11.1-3 (1984) Abstract only.
Moskvitin, Physiocochemical Principles of Gluing and Adhesion processes, NSF, Rpt. No. SFCSI-Agr (TT-68-50368, p. 197 (1969) Abstract only.
Mayne, "Further developments with epoxy/polyamine films," Corros. Sci., vol. 35, Nos. 5/8, pp. 1359-1361 (1993) Abstract only.
Padday, "Spreading, wetting, and contact angles," J. Adhes. Sci. Tech., vol. 6, No. 12, pp. 1347-1358 (1992) Abstract only.
Mark, "Future improvements in cohesive and adhesive strength of polymers. I.," Adhesives Age, vol. 22, No. 7, pp. 35-40 (1979) Abstract only.
Hansen, "The three dimensional solubility parameter—key to paint component affinities: I. Solvents, Plasticizers, Polymers, and Resins," Journal of Paint Technology, vol. 39, No. 505, pp. 104-117 (1967).

Hansen, "The three dimensional solubility parameter—key to paint component affinities: II and III—II. Solvents, Plasticizers, Polymers, and Resins," Journal of Paint Technology, vol. 39, No. 511, pp. 505-510 (1967).

Hansen, "III. Independent calculation of the parameter components," Journal of Paint Technology, vol. 39, No. 511, pp. 511-514 (1967).

Hansen et al., "On the use of cohesion parameters to characterize surfaces," J. Adhesion, vol. 15, pp. 275-286 (1983).

Hansen, "Cohesion parameters for surfaces, pigments, and fillers," Surface Coatings International vol. 8, pp. 386-391, (1997).

Shareef et al., "Suspension interaction of pigments in solvents: characterization of pigment surfaces in terms of three-dimensional solubility parameters of solvents," Journal of Coatings Technology, vol. 58, No. 733, pp. 35-44 (1986).

Vinther, "Application of the concepts solubility parameter and pigment charge," Chemie des Peintures Engl. vol. 34, No. 10, pp. 363-372 (1971).

Schreiber, "Solvent balance, dispersion and rheological properties of pigmented polymer compositions," Journal of Paint Technology, vol. 46, No. 598, pp. 35-39 (1974).

Burrell, "The challenge of the solubility parameter concept," Journal of Paint Technology, vol. 40, No. 520, pp. 197-208 (1968).

Trudgian, "The pattern of solvent-resin-pigment affinities," Official Digest, Presented at the 41$^{st}$ Annual Meeting of the Federation of Societies for Paint Technology, pp. 1210-1231 (1963).

Schroder, Colloid chemistry aids to formulating inks and paints, Harmonization of the energetics of raw materials by using the solubility parameter concept, vol. 5, No. 98, pp. 334-340 (no date).

Chasey, "Methods for evaluating oil/polymer interactions in carbon black filled compounds," Rubber World, pp. 35-40 (1993).

Wolff, et al., "Filler-elastomer interactions. Part VII. Study on bound rubber," Rubber Chemistry and Technology, vol. 66, No. 2, pp. 163-177 (1993).

Barton, "CRC Handbook of solubility parameters and other cohesion parameters," pp. 1-21, (1991).

Kaya, et al., "Interfacial parameters and work of adhesion in soil-liquid systems," Geotechnical Testing Journal, vol. 23, No. 4, pp. 464-471 (2000).

Skaarup, "The three dimensional solubility parameter and its use—II. Pigmented Systems," pp. 28-42 (no date).

Grubenmann, "The solvent dependence of the solubility of organic solids, and solubility parameter theory: investigation by means of an organic pigment," Dyes and Pigments, vol. 21, pp. 273-292 (1993).

"Bound Rubber and Carbon Black Reinforcement," by E. M Dannenberg, 1986, pp. 512-524.

"Filler-Elastomer Interactions. Part VII. Study on Bound Rubber," by Siegfried Wolff et al., reprinted from Rubber Chemistry and Technology, vol. 66, No. 2, May-Jun. 1993, 163-177.

"Standard Test Method for Carbon Black—Iodine Adsorption Number," ATSM Designation D 1510-99, pp. 271-275.

"Standard Test Method for Carbon Black—CTAB (Cetyltrimethylammonium Bromide) Surface Area," ATSM Designation D 3765-99, pp. 563-568.

"Standard Test Methods for Carbon Black—Surface Area by Multipoint B.E.T. Nitrogen Adsorption," ATSM Designation D 4820-97, pp. 763-769.

"Standard Test Methods for Carbon Black—External Surface Area by Multipoint Nitrogen Adsorption," ATSM Designation D 5816-96, pp. 878-880.

"Standard Test Method for Carbon Black—Total and External Surface Area by Nitrogen Adsorption," ATSM Designation D 6556-00a, pp. 970-974.

"Roles of Work of Adhesion between Carbon Blacks and Thermoplastic Polymers on Electrical Properties of Composites," by Soo-Jin Park et al., published in the Journal of Colloid and Interface Science 255, pp. 145-149 (2002).

"Component Interactions and the Stability of Some Pigment/Polymer Dispersions," by P. Mukhopadhyay et al., published in the Journal of Applied Polymer Science, vol. 67, pp. 245-253 (1998).

"Adhesion and Components of Solid Surface Energies," by John H. Clint, published in Current Opinion in Colloid & Interface Science 6, pp. 28-33 (2001).

"Estimation of the Reliability of Hansen-Parameters of Photooxidative Degraded Polymer Films by Contact Angle Measurements," by Anita Horn et al., Hildesheim, Germany, pp. 1-12.

"Basic and Acidic Surface Oxides on Carbon Fiber and Their Influence on the Expected Adhesion to Polyamide," by A. Bismarck et al., published in Colloids and Surfaces, A: Physiochemical and Engineering Aspects 159, pp. 341-350 (1999).

International Preliminary Report on Patentability and Written Opinion of the International Searching Authority for International Patent Application No. PCT/US2004/010267 dated Oct. 13, 2003.

Declaration of Non-Establishment of International Search Report for PCT/US2004/010268, dated Mar. 1, 2005.

Hodne et al., "The Effect of the Cement Zeta Potential and Slurry Conductivity on the Consistency of Oilwell Cement Slurries," Cement and Concrete Research, vol. 30, pp. 1767-1772, 2000.

* cited by examiner

Figure 1. Wc-Wa calculation used to predict the weight percent carbon needed in a HDPE composite to achieve $10^3$ ohms/cm resistivity for 7 different carbon black particles Figure 2. Wc-Wa calculation used to predict the weight percent carbon needed in a polyamide composite to achieve $10^3$ ohms/cm resistivity for 5 different carbon black particles.

Figure 3. Wc-Wa calculation used to predict the weight percent carbon needed in a HDPE composite to achieve impact resistance of 20kJ/m2 (diamonds) and 25kJ/m2 (squares) for 7 different carbon black particles.

Figure 4. Wc-Wa calculation used to predict the weight percent carbon needed in a polyamide composite to achieve impact resistance of 20kJ/m2 (diamonds) and 25kJ/m2 (squares) for 5 different carbon black particles

METHODS OF SELECTING AND DEVELOPING A PARTICULATE MATERIAL

The present application claims the benefit under 35 U.S.C. Section 119(e) of U.S. Provisional Patent Application Nos. 60/491,632 filed Jul. 31, 2003; 60/485,965 filed Jul. 10, 2003; 60/485,964 filed Jul. 10, 2003; and 60/459,230 filed Apr. 1, 2003; and 60/497,592 filed Aug. 25, 2003 which are incorporated in their entirety by reference herein. The present invention relates to methods for selecting or developing particulate materials for a composition or application. The present invention also relates a collection of particulate materials or a group of particulate materials based on interfacial potential property values. The descriptions set forth in U.S. Provisional Patent Application Nos. 60/491,632; 60/485,965; 60/485,964; and 60/459,230; and 60/497,592 are incorporated in their entirety by reference herein.

BACKGROUND OF THE INVENTION

In general, products of the chemical industry fall into one of two types—formulaic chemicals and performance chemicals. Formulaic chemicals are defined by their composition. If they are sold in different grades, the grades are distinguished by the concentration of impurities. Examples include ammonia, benzene, carbon tetrachloride, diethyl ether, formaldehyde, soda ash, and calcium oxide. Performance chemicals, which include polymers, dyes, pigments, and fragrances, are valued because of what they do, not what their composition is. Important types of performance chemicals include fine particle products such as carbon black, silica, titania, tantalum, calcium carbonate which are used in applications including reinforcement, rheology, color, and conductivity.

Fine particles are used to enhance such properties of compound materials as rheology, flow, strength, color, etc. The ability of the fine particle product to achieve the desired level of performance depends upon particle characteristics. In order to differentiate classes of performance, types or grades are commonly defined. These definitions include the designation of certain particle properties and the assignment of typical or target values for those properties. Prior to the present invention, the particle properties have been related to morphology; e.g. particle size, particle size distribution, particle shape or structure, and the like.

In order to insure consistency, specifications are set for fine particle products. Typically these specifications will include one or more measures of morphology and may further include one or more measures of chemical constituents. Common measures of morphology are particle size, surface area, structure, porosity, aggregate size, and aggregate shape. Common measures of chemistry include bulk and surface composition as well as analyses of extractable species. Measurements of variability of these properties can be made either during manufacturing to insure the process remains in control (often referred to as quality control, or QC) or on the product prior to shipment (often referred to as quality assurance, or QA).

For example, carbon black is typically sold with at least one morphological specification, which may be surface area, particle size, structure, and porosity. Performance tests, such as, for example, bound rubber or compound moisture absorption (CMA) tests may also be run, depending on the intended use for the carbon black. However, these are not typically included on a product specification sheet.

Despite these quality control and quality assurance (QC/QA) efforts, it is not unusual for a customer to complain that a batch of product received did not perform as expected, despite being "within spec". For example, variations in the rate of rubber cure, the appearance of white haze on molded rubber parts, low thixotropy in adhesives, and variations in plastic compounding times have all been traced back to lot-to-lot variations of carbon blacks even when each lot was within specification. This often results in the producer undertaking a thorough and costly study of the process and product and trying to make adjustments so that the product once again performs as expected. Since there can be such variation in product performance for particulate materials, it is difficult for a customer or particulate manufacturer to select the best particulate for the composition. How can the product performance be at its best, when the particulate material and its interactions in the composition are not fully appreciated or understood? The present invention permits one to achieve improved performance by providing a better appreciation, a better understanding, and a better selection of particulate materials.

Determining why a product did not perform as expected is inefficient and often both time consuming and expensive. It involves evaluation to assess why a problem has occurred rather than avoiding the problem in the first place. Many times, the producer will adjust manufacturing steps, not understanding the result but only in an attempt to change the product somehow to see a product difference. At times, this amounts to guess work.

Since performance of the particulate materials in a composition can be a problem as explained above, there is a need to develop means to select particulate material to optimize the performance in a matrix or composition to avoid or minimize the above-described problems. Also, there is a need to develop an improved system for allowing the proper or optimal selection of particulate materials for a matrix or composition, for instance, that will permit an improved or optimized performance in an application.

SUMMARY OF THE INVENTION

The present invention relates in part to a method of selecting a candidate particulate material for a composition comprising a particulate material and a matrix, wherein the method comprises the step of selecting the candidate particulate material based on a predetermined relationship between:
  A) at least one performance property of the composition and
  B) 1) at least one homogeneous interaction parameter for the particulate material, or
  B) 2) at least one homogeneous interaction parameter for the particulate material and at least one heterogeneous interaction parameter for the particulate material and the matrix. The homogeneous interaction parameter may comprise at least one interfacial potential property value, at least one value derived from an interfacial potential property value, at least one component of an interfacial potential property value, or combinations thereof for the particulate material and the heterogeneous interaction parameter may comprise at least one interfacial potential property value, at least one value derived from an interfacial potential property value, at least one component of an interfacial potential property value, or combinations thereof for the particulate material and for the matrix.

The present invention further relates to a method of selecting a candidate particulate material for a composition comprising a particulate material and a matrix, wherein the method comprises the step of selecting the candidate particulate material based on a predetermined relationship between:
  A) at least one performance property of a composition comprising the particulate material and a surrogate matrix, and
  B) 1) at least one homogeneous interaction parameter for the particulate material or
  B) 2) at least one homogeneous interaction parameter for the particulate material and at least one heterogeneous interaction parameter for the particulate material and the matrix. The homogeneous and heterogeneous interaction parameters may be as described above.

The present invention further relates to a method of providing a candidate particulate material for a composition comprising a particulate material and a matrix, wherein the method comprises the steps of:

A) providing at least one probe particulate material having a predetermined interfacial potential property value, value derived from an interfacial potential property value, component of an interfacial potential property value, or combinations thereof to a customer;

B) selecting the candidate particulate material based on a predetermined relationship between
  a) at least one performance property of the composition and
  b) 1) at least one homogeneous interaction parameter for the particulate material or
  b) 2) at least one homogeneous interaction parameter for the particulate material and at least one heterogeneous interaction parameter for the particulate material and the matrix; and C) providing the candidate particulate material to the customer.

The present invention further relates to a composition comprising a particulate material and a matrix, wherein the composition has at least one performance property that is related to the combination of:

A) at least one homogeneous interaction parameter for the particulate material or B) at least one homogeneous interaction parameter for the particulate material and at least one heterogeneous interaction parameter for the particulate material and the matrix.

The present invention further relates to a method of providing a performance property comprising the step of combining a particulate material and a matrix, wherein the particulate material and the matrix have at least one interfacial potential property value, value derived from an interfacial potential property value, component of an interfacial potential property value, or combinations thereof which is related to the performance property.

The present invention further relates to a method of selecting a candidate matrix for a composition comprising a particulate material and a matrix, wherein the method comprises the step of selecting the candidate matrix based on a predetermined relationship between:

A) at least one performance property of the composition and

B) 1) at least one homogeneous interaction parameter for the particulate material or B) 2) at least one homogeneous interaction parameter for the particulate material and at least one heterogeneous interaction parameter for the particulate material and the matrix.

The present invention further relates to a method of developing a new or improved particulate material, wherein the method comprises the step of obtaining at least one trend and/or functional relationship between:

A) at least one performance property of two or more compositions, each of said compositions comprising a matrix and a particulate material, and B) 1) at least one homogeneous interaction parameter for the particulate material or B) 2) at least one homogeneous interaction parameter for the particulate material and at least one heterogeneous interaction parameter for the particulate material and the matrix. The method may further comprising the step of making said new or improved particulate material having the identified interfacial potential property value, value derived from an interfacial potential property value, component of an interfacial potential property value, or combination thereof.

The present invention further relates to a method of developing a new or improved composition comprising a matrix and a particulate material, wherein the method comprises the step of obtaining at least one trend and/or functional relationship between A) at least one performance property of two or more compositions, each of said compositions comprising the matrix and a particulate material, and B) 1) at least one homogeneous interaction parameter for the particulate material or B) 2) at least one homogeneous interaction parameter for the particulate material and at least one heterogeneous interaction parameter for the particulate material and the matrix.

The present invention further relates to a performance map comprising

A) at least one performance property of a composition comprising a matrix and a particulate material, and B) 1) at least one homogeneous interaction parameter for the particulate material or B) 2) at least one homogeneous interaction parameter for the particulate material and at least one heterogeneous interaction parameter for the particulate material and the matrix. Preferably the performance map demonstrates at least one trend and/or functional relationship between A) and B). In addition, the present invention relates to a method of developing a new and/or improved particulate material or composition utilizing this performance map.

The present invention further relates to a method of performance mapping comprising the step of comparing between A) at least one performance property of a composition comprising a matrix and a particulate material, and B) 1) at least one homogeneous interaction parameter for the particulate material or B) 2) at least one homogeneous interaction parameter for the particulate material and at least one heterogeneous interaction parameter for the particulate material and the matrix.

The present invention further relates to a process map comprising

A) at least one interfacial potential property value, at least one value derived from an interfacial potential property value, at least one component of an interfacial potential property value, or combinations thereof for a particulate material and B) at least one process variable for a process for preparing said particulate material.

Preferably, the process variable is temperature, pressure, chemical composition, residence time, stoichiometry, reactor quench length, amount of quench air, feedstock composition, primary fuel type, type and/or level of downstream additives, or type, concentration, and/or amount of post treatment. The type of post treatment can be chemical modification or addition of an adherent, such as a surfactant or dispersant. In addition, the present invention relates to a method of developing a new and/or improved particulate material or composition utilizing this process map.

The present invention further relates to a method of process mapping comprising the step of comparing between
A) at least one interfacial potential property value, at least one value derived from an interfacial potential property value, at least one component of an interfacial potential property value, or combinations thereof for a particulate material and
B) at least one process variable for a process for preparing said particulate material.

It is to be understood that both the foregoing general description and the following detailed description are exemplary and explanatory only and are intended to provide further explanation of the present invention, as claimed.

DETAILED DESCRIPTION OF THE INVENTION

Figure 1:
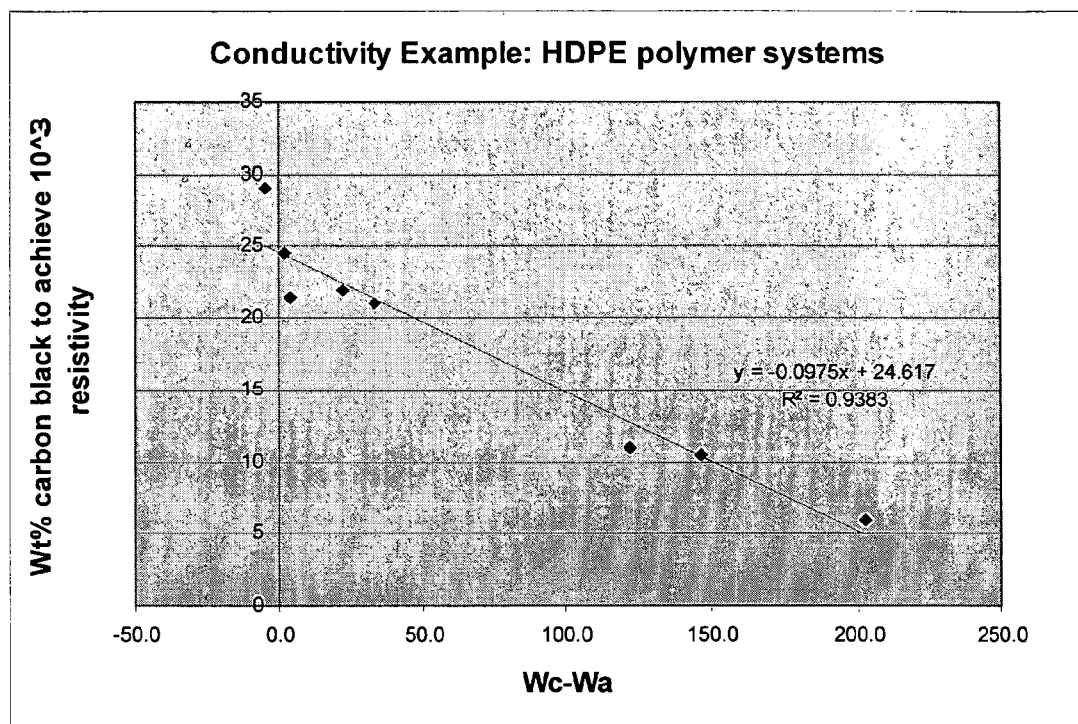
FIGS. 1-4 and 6 are graphical representations of relationships between performance properties and at least one interfacial potential property value, at least one value derived from an interfacial potential property value, at least one component of an interfacial potential property value, or combinations thereof for the particulate materials.

In the area of particulate materials and in the area where manufacturers incorporate particulate materials in compositions such as polymers and other matrices, there is a continuing effort to select the best candidate of particulate materials for the composition based on desired performance. In the past, the means for selecting a particulate material for use in a composition to achieve a desired performance was based on the morphology of the particulate material and/or the chemistry of the particulate material. Even knowing these parameters, selecting a particulate material for incorporation in a composition to achieve a desired performance still resulted in some unpredictability and involved a certain amount of guess work. There is a desire in the industry for methods and systems that will provide a more accurate way to select candidate particulate materials for use in compositions and lead to an improved performance, or the desired performance.

The present invention provides such a method and system which allows one to select a candidate particulate material for a composition and preferably provide improved or optimized performance properties in the composition. The present invention makes use of the interfacial potential of the particulate material either alone or in combination with the interfacial potential of the matrix in which the particulate material is used. Thus, the present invention includes the use of at least one homogeneous interaction parameter for the particulate material (for example, the work of cohesion of a particulate material) or at least one homogeneous interaction parameter for the particulate material in combination with at least one heterogeneous interaction parameter for the particulate material and the matrix (for example, the work of cohesion and the work of adhesion).

A "homogeneous interaction parameter" relates to how the particulate material interacts with itself. A "heterogeneous interaction parameter" relates to how the particulate material and the matrix interact with each other. In general, it is known that performance properties of compositions comprising a particulate material and a matrix may depend on how the particulate material and matrix interact. Thus, performance has been related to heterogeneous interactions. However, it has now been surprisingly found that performance properties depend on either the interaction of the particulate material with itself alone or a balance between that homogeneous interaction and the particulate material's interaction with the matrix (a heterogeneous interaction). The embodiments of the present invention take advantage of this relationship. Based on this, it has been found that, by utilizing a homogenous interaction parameter for the particulate material, as disclosed in the present invention, either alone or in combination with a heterogeneous interaction parameter, a more accurate selection can be made for the particulate material. In each of the embodiments discussed herein, the term "interfacial potential value" or "interfacial potential" refers to a characterization of the particulate material or the matrix. Interfacial potential property values are determined by the interaction of the particle with a specified system. The term "homogeneous interaction parameter" may comprise at least one interfacial potential property value (i.e., a measured or calculated value which relates to interfacial potential), at least one value which can be derived or calculated from an interfacial potential property value (for example, work of cohesion), at least one component of an interfacial potential property value (such as an acidic component, a basic component, or a dispersive component), or combinations thereof for the particulate material. The term "heterogeneous interaction parameter" may comprise at least one interfacial potential property value, at least one value derived from an interfacial potential property value, at least one component of an interfacial potential property value, or combinations thereof for both the particulate material and for the matrix. Throughout, the term "combination" refers to both a mathematical combination (such as the difference or ratio) as well as a combined use (such as in a multi-dimensional graph or other visual representation).

In more detail, and in one embodiment, the present invention involves, in part, a method of selecting a candidate particulate material for a composition comprising a particulate material and a matrix, wherein the method comprises the step of selecting the candidate particulate material based on a predetermined relationship between:
A) at least one performance property of the composition and
B) 1) at least one homogeneous interaction parameter, such as an interfacial potential property value, value derived from an interfacial potential property value, component of an interfacial potential property value, or combinations thereof, for the particulate material, or
B) 2) a combination of at least one homogeneous interaction parameter for the particulate material and at least one heterogeneous interaction parameter, such as an interfacial potential property value, value derived from an interfacial potential property value, component of an interfacial potential property value, or combinations thereof, for the particulate material and for the matrix. The selected candidate particulate material can have an interfacial potential property value, value derived from an interfacial potential property value, component of an interfacial potential property value, or combinations thereof) which results in a target value for the performance property of the composition. The method can further include the step of determining the relationship between A) and B) or the relationship can be previously determined. The method can further include the step of determining the interfacial potential property value, the value derived from an interfacial potential property value, the component of an interfacial potential property value, or combinations thereof for the matrix. As an option, the step of determining the interfacial potential property value, the value derived from an interfacial potential property value, the component of an interfacial potential property value, or combinations thereof for the matrix can involve determining the performance property of a composition comprising the matrix and at least one probe particulate material having a predetermined interfacial potential property value, value derived from an interfacial potential property value, component of an interfacial potential property value, or combinations thereof.

The method can involve the step of determining the interfacial potential property value, value derived from an interfacial potential property value, component of an interfacial potential property value, or combinations thereof for the matrix by determining a surrogate matrix having a predetermined interfacial potential property value, value derived from an interfacial potential property value, component of an interfacial potential property value, or combinations thereof. The method can further include the step of selecting the candidate particulate material based on a predetermined relationship between:

A) at least one performance property of a composition comprising the surrogate matrix and the particulate material, and B) a combination of
  i) at least one interfacial potential property value, at least one value derived from an interfacial potential property value, at least one component of an interfacial potential property value, or combinations thereof for the particulate material and
  ii) at least one interfacial potential property value, at least one value derived from an interfacial potential property value, at least one component of an interfacial potential property value, or combinations thereof for the surrogate matrix. This relationship can be predetermined or the method can include the step of determining the relationship between A) and B).

The present invention also relates to a method of providing a candidate particulate material for a composition comprising a particulate material and a matrix, wherein the method comprises the steps of:

A) providing at least one probe particulate material having a predetermined interfacial potential property value, value derived from an interfacial potential property value, component of an interfacial potential property value, or combinations thereof to a customer;

B) selecting the candidate particulate material based on a predetermined relationship between
  a) at least one performance property of the composition and
  b) 1) at least one homogeneous interaction parameter, such as at least one interfacial potential property value, value derived from an interfacial potential property value, component of an interfacial potential property value, or combinations thereof for the particulate material or
  2) a combination of at least one homogeneous interaction parameter, such as at least one interfacial potential property value, value derived from an interfacial potential property value, component of an interfacial potential property value, or combinations thereof for the particulate material and at least one heterogeneous interaction parameter, such as at least one interfacial potential property value, value derived from an interfacial potential property value, component of an interfacial potential property value, or combinations thereof for the particulate material and for the matrix; and C) providing the candidate particulate material to the customer.

In this method, the selected candidate particulate material can have an interfacial potential property value, value derived from an interfacial potential property value, component of an interfacial potential property value, or combinations thereof which results in a target value for the performance property of the composition. As stated previously, the method can further involve the step of determining the relationship between A) and B).

In one embodiment of the present invention, the method of the present invention permits one to select a particulate material that will provide the same or similar performance properties than a more expensive particulate material. In other words, the present invention will permit one to select a candidate particulate material that has a lower cost than a second candidate particulate material, wherein the candidate particulate material and second candidate particulate material have similar interfacial potential property values, values derived from an interfacial potential property value, components of an interfacial potential property value, or combinations thereof and result in similar target values for the performance property of the composition.

The present invention further relates to a collection of particulate materials which is based upon the interfacial potentials for each particulate material. In this embodiment, various particulate materials (e.g., two or more types) are grouped or ranked together based on at least one interfacial potential property value, at least one value derived from an interfacial potential property value, at least one component of an interfacial potential property value, or combinations thereof for each particulate material. The collection or ranking provides a selection key or selection guide of particulate materials having various interfacial potential property values. By providing such a collection or ranking of particulate materials, this collection or ranking can, for instance, be provided to a customer to assist them in the selection process for a candidate particulate material for a composition.

The present invention further involves an ordering of at least two particulate materials which is based on at least one interfacial potential value for each particulate material. The ordering of at least two particulate materials based on an interfacial potential value system permits, for instance, a customer to select a proper or most optimal candidate particulate material for use in a composition to provide, for instance, preferred performance properties. The ordering of the particulate materials, for instance, based on increasing or decreasing interfacial potential will assist a customer or particulate material manufacturer with deciding on what is the best particulate material for a composition. By providing an ordering of at least two particulate materials, the selection process can more easily be accomplished. For instance, if one particulate material provides improved performance compared to the previously used particulate material, then the ordering of at least two or more particulate materials will provide a customer with the ability to select the next particulate material in the order to test for performance property of the composition. The ordering of the particulate material can be represented in any fashion such as by graph, table, or other representations. The ordering of the particulate material can be based on two or more particulate materials such as at least 3, at least 5, at least 10, at least 50, or at least 100 particulate materials. Essentially, this ordering of particulate materials permits a library of particulate materials based on interfacial potential values and optionally other parameters such as morphology and/or chemical parameters. This ordering of particulate materials permits one to utilize this ordering to pick a particulate material for a particular matrix. Furthermore, the ordering of particulate materials permits one to utilize the ordering to pick a particulate material for a particular application such as, for conductivity, and ultimately in end use applications such as toners, coatings, inks, other polymer applications, and the like.

With the present invention, the manufacturer and/or customer have a better way to systematically select particulate materials. With the present invention, one can create a roadmap on what particulate materials to test for performance properties and what should be the next particulate material to test for performance. By ordering the particulate materials based in part on the interfacial potential(s), one can logically decide which particulate material should be tested next.

Thus, the present invention includes, as an embodiment, a grouping of at least two particulate materials that have predetermined interfacial potential property values, such as values derived from an interfacial potential property value, components of an interfacial potential property value, or combinations thereof, in a particular matrix. The grouping of the particulate materials can have the same or different interfacial potential property values. The grouping of the particulate materials can have interfacial potentials that are the same and wherein at least on morphological and/or chemical parameter is different. In the alternative, the grouping of the particulate materials can have at least one morphological and/or chemical value that is the same and wherein the values for the interfacial potential are different. Thus, any combination of properties is possible with respect to this grouping of particulate materials. With this ability to group particulate materials in an organized fashion based on, in part, interfacial potential property values, the present invention further permits a sampling kit or collection to be provided to a customer. The sampling kit or collection includes at least two particulate materials having predetermined interfacial potentials. This sampling kit can have two or more types of particulate materials. This kit will permit customers to test various particulate materials in compositions to determine what is the best candidate for the desired performance properties of the composition. This sampling kit, since it is based, in part, on the interfacial potentials of each particulate material, will provide a more accurate and more informative way for a customer to best optimize or improve upon candidate particulate materials for a given composition. Unlike any previous sampling done in the industry, this sampling collection and sampling method provides a more focused system to properly and accurately select the best or optimal particulate material for a composition. This system and method can work with improving previously determined compositions or with respect to providing a customer a sampling collection for a composition that is being prepared for the first time.

For purposes of the present invention, as used herein, the term "value" includes a specific number or value or multiple numbers or values, or a range of numbers or values.

Particulate materials such as fillers and pigments are made within defined specifications but even doing so it has been found that the product at times would not perform consistently in the customer's application. Until now, the industry was not entirely clear why the product would not perform consistently even though it was within morphological specifications. The present invention now makes it possible to select particulate materials based on at least one homogeneous interaction parameter for the particulate material, either alone or in combination with at least one heterogeneous interaction parameter for the particulate material and the matrix which enables a customer to more readily achieve the desired performance of their product. In this way, the customer is provided with a product that should perform consistently and optimally in their end product. The present invention also provides a way to better select types, grades, and/or brands of particulate material. This system permits the manufacturers and customers to better select types, grades, and/or brands of particulate materials and permits those in the industry to select more accurately the types, grades, and/or brands of particulate materials.

A particulate material is generally made available in a variety of units, including batches, lots, samples, shipments, and the like. Typically, a customer and/or a supplier will agree on specifications for that unit of product, which may be included in a contractual agreement, including an oral agreement, purchase order, invoice, contract, waiver to a contract, or combinations thereof. The method of the present invention involves the step of selecting a certain particulate material based on at least one homogeneous interaction parameter for the particulate material, either alone or in combination with at least one heterogeneous interaction parameter for the particulate material and a matrix. Furthermore, the method of the present invention may also include the step of selecting based at least one morphological value and/or at least one chemical value of the particulate material.

For each of the embodiments of the present invention, any particulate material may be used. The particulate material may be in any form such as a powder, a pellet, or a fluffy material. Examples of particulate materials include, but are not limited to, fillers, extenders, carbonaceous materials, carbon black, inorganic salts, silica (such as fumed silica, precipitated silica, or colloidal silica), silica aerogels, fumed oxides, silicates, silica sols including Stöber sols, metal oxides, hydrous metal oxides, iron oxides, aluminum oxides, boehmite, aluminum silicates, clays, kaolin, halloysite, montmorillonite, attapulgite, zeolites, ceramics (such as a metal carbide, a metal nitride, or a metal boride), calcium carbonate, chalk, barium sulfate, diatomaceous earth, asbestos, pigments (such as phthalocyanines, Prussian blue, chromium oxide, and chrome green), zinc sulfide, zinc oxide, titania, antimony oxide, lead zinc, metals (such as tantalum, niobium, copper, silver, platinum, iron, aluminum, copper, silver, gold, platinum, or silicon), metal alloys, and any of the above with surface treatments such as hydrophobic silicas, surface-modified carbon blacks, polymer treated powders, and laked pigments. Combinations or mixtures of these particulate materials may also be used. Examples of carbonaceous materials include, but are not limited to, carbon black, graphite, vitreous carbon, activated carbon, buckeyballs, carbon fibers, nanotubes, graphite, and the like. Other examples include aggregates containing a carbon phase and a silicon-containing species phase or an aggregate containing a carbon phase with a metal-containing species phase. Also, coated particulate materials, such as silica-coated carbon black are other examples of particulate material. Furthermore, the carbonaceous material or other particulate material can be modified in any way such as having attached organic groups, polymer groups, and the like. Examples may include those described in U.S. Pat. Nos. 5,747,562, 5,830,930, 5,877,238, 5,904,762, 5,916,934, 5,919,841, 5,948,835, 6,008,272, 6,017,980, 6,028,137, 6,057,387, 6,197,274, 6,211,279, 6,323,273, 6,364,944, 6,448,309, all of which are incorporated in there entirety by reference herein.

Furthermore, for each of the embodiments of the present invention, the matrix may be any system into which a particulate material can be added. For example, the matrix may comprise at least one polymer, solvent, colorant, surfactant, additional particulate material, or combinations thereof. Preferably the matrix is a solvent or a polymer. Examples of polymeric matrices include natural rubber, cellulose, fluoropolymers, polyamides, and homo- and copolymers of butadiene, ethylene, propylene, acrylonitrile, vinyl chloride, vinyl acetate, (meth)acrylate monomers, styrene, oxymethylene, and ethylene terephthalate. Examples of solvents include both aqueous vehicles and non-aqueous vehicles.

Particulate materials are used in a variety of compounded systems, including, for example, dispersions in elastomers, polymers, solvents, resins, or mixtures thereof. Important aspects of performance include reinforcement, rheology control, formation of percolating networks, degree of dispersion, color, and conductivity. The properties of these compound systems are derived, in part, from the morphology of the particulate material used. Other physical phenomena involving particulate materials may respond to interfacial potential properties. Some also respond to the combination of both. Therefore, since interfacial potential plays an important role for particulate materials, along with morphology, the method of the present invention comprises utilizing at least one homogenous interaction parameter, which reflects the interfacial potential of the particulate material, either alone or in combination with at least one heterogeneous interaction parameter, which reflects the interfacial potential of the particulate material and of the matrix. In this way, it has unexpectedly been found that products are better characterized, better identified, better selected, and more easily developed, particularly for a customer. Such a parameter and system enables better selection of the optimal particulate material for its use in a composition.

The interfacial potential of a particulate material is defined through a measure of a physical phenomenon that depends on the interaction of particulate material with other materials or with itself, after the effects of morphology have been removed. When two particles are in contact with each other the interfacial potential is the cohesion per unit area of contact. When particulate material is mixed into a fluid, the interfacial potential is the adhesion per unit area of the particle. If the measurement is per unit mass then the total interaction depends on the surface area per unit mass and the interfacial potential per unit area.

Examples of phenomena that relate solely to interfacial potential include the partitioning of particles between liquid phases, the spreading pressure of adsorbed gas, and the drop contact angle. These phenomena can be measured and the results applied without ambiguity as to whether the result is from morphology or interfacial potential since they only depend on interfacial potential.

However, as stated above, many useful physical phenomena respond to both morphology and interfacial potential. The morphology of a particulate material is a description of its shape, size, and structure. The morphology can include particle size, surface area, particle porosity, aggregate size, aggregate shape, maximum packing density, powder bed porosity. In addition, the morphological value can include characteristics of a distribution, such as mean, standard deviation, width, skewness, etc., of such values as particle size, pore size, aggregate size, etc. A morphological value is the result of a measurement of one of these characteristics, or combinations thereof. The surface area per unit mass, the single particle diffusion constant, the average diameter of primary particles, and microstructure such as the diameters, shapes, and number of pores are examples of morphological values.

Examples of phenomena that respond to both morphology and interfacial potential include most aspects of rheology (e.g. yield, viscosity and shear thinning), the wicking rate of fluids in powder columns, and the maximum torque and the fluid volume at which it occurs in stirring wetted powders (i.e. the absorptometer or oil absorption test). For example, the rate a fluid rises in a column of packed particles depends upon both the pore size distribution of the column and the strength of the wetting interaction per unit area between the fluid and the particle surface. The volume at which the maximum torque occurs depends upon the maximum density to which the powder can be packed and the strength of the capillary forces in compressing the powder. The capillary forces, in turn, depend on the pore size and the interfacial potential per unit area. If the interaction is large enough and/or the pores small enough, the particulate material will be compressed to or nearly to its maximum density. Thus, for absorptometry on some particulate materials with some liquids, the characteristic volume is determined solely by particle morphology. For other liquids, volume and torque are determined by morphology and interfacial potential.

While these phenomena result from both morphological as well as interfacial potential effects, the way in which the measurements are analyzed, i.e., the calculation or algorithm used, will determine whether it is a morphological value or an interfacial potential property value. Thus, it is possible to use a test that responds to both morphology and interfacial potential and obtain independent information about both.

For example, a subset of physical phenomena that respond to both morphology and interfacial potential are ones where the only relevant aspect of the morphology is surface area and the dependence on area is known. Typical examples of this type of phenomena are adsorption studies where the partitioning of trace molecules between the surface and a gas or liquid phase is determined. For these physical phenomena the measurement is adjusted for surface area and the interfacial potential calculated.

Another subset of physical phenomena that responds to both morphology and interfacial potential are ones where the dependence on morphology and interfacial potential can be separated by mathematical analyses. For example the amount of gas adsorbed as a function of the pressure depends on the surface area and the interfacial potential. This function and the known size of the gas molecule can be used to calculate either the surface area or the interfacial potential. The calculation of surface area using nitrogen gas is the so-called BET method. The usual calculation gives the surface area, an aspect of morphology, and the method is a morphological method. A different calculation gives the interfacial potential and the method is therefore an interfacial potential method.

Some physical phenomena may be separated into morphological effects and interfacial potentials by an algorithm. These provide a basis for measuring either morphology or interaction potential. The algorithm by which the data are interpreted determines which type of measurement it is.

A phenomenon that responds to both morphology and interfacial potential may be used to assign an interfacial potential property value to a particulate material if one of the following conditions is met.

A) if the effect of morphology can be eliminated by also measuring the physical phenomena with an inert probe. An inert probe is one for which the interfacial potential is negligible. For example, in inverse gas chromatography (IGC) the retention time of an inert probe is also measured.

B) if an external parameter, such as pressure or temperature, is changed and the response to that parameter allows an independent calculation of one or more morphological and interfacial potential values. For example, the BET analysis records adsorption as a function of pressure and two constants are calculated from the data. One constant measures surface area and one interfacial potential.

C) if the physical phemonenon is measured with the same particulate material in different fluids. The results are compared to determine differences when morphology of the particles is the same. The differences are derived from the different interfacial potentials. For example, the rate of wicking of various liquids can be compared to the rate of wicking of a hydrocarbon through a similarly packed powder bed.

D) if the number of different tests, which respond to both morphology and interfacial potential, exceeds the number of morphological parameters of concern minus those that have been determined by independent tests, then there are a sufficient number of independent tests to insure the consistency of the morphological parameters, plus at least a single aspect of the interfacial potential.

In all these, with the exception of D), the common purpose is to identify the portion of a physical phenomenon that depends on the interaction of particulate materials with other materials or with itself after the effects of morphology have been removed. This portion is the interfacial potential.

Therefore, each of the embodiments of the method of the present invention, may utilize or include any of the techniques described above. Others are described in more detail below.

As described earlier, the method of the present invention may further comprise the step of selecting based also on at least one morphological value. The morphological values may be any of those described above and can be determined using any method known in the art, such as colloidal techniques, including liquid or vapor adsorption, microscopy, or combinations of thereof. Typical liquid or vapor probes for adsorption include nitrogen, iodine, cetyltrimethyl ammonium bromide (CTAB), dibutyl phthalate (DBP), or paraffin oil. Previously, the adsorptions of nitrogen, iodine, and cetyltrimethylammonium bromide (CTAB) have been used to measure the surface area of carbon blacks (e.g., ASTM D4820, D5816, and D6556 for nitrogen adsorption; D1510 for iodine number, and D3756 for CTAB area). The surface area should be the same by all techniques, but for some carbon blacks the surface areas are not the same. These differences were attributed to differences in porosity or other morphological properties. Examples of useful microscopy techniques include, but are not limited to, transmission electron microscopy (TEM), X-ray diffraction, dark field microscopy, oxidation studies, diffracted beam electron microscopy, phase contrast transmission electron microscopy imaging, high resolution scanning electron microscopy (SEM), scanning tunneling electron microscopy (STEM), scanning tunneling microscopy (STM), scanning force microscopy (SFM), and atomic force microscopy (AFM) imaging. Examples of colloidal techniques include, but are not limited to, masstone (blackness or color), tinting strength (ASTM D 3265), and the adsorption of nitrogen gas data (ASTM D 3037), cetyltrimethyl ammonium bromide (ASTM D 3765), or iodine (ASTM D 1510). The surface areas derived from each of the above mentioned methods can be affected in different ways by the amount and type of porosity, as well as the chemical nature of the surface of the particulate material. Porosity can be estimated from the apparent extra surface area detected in the adsorption of small probes, e.g., nitrogen, over large probes, e.g., CTAB. The aggregate size can be estimated by TEM, disc centrifuge photosedimentometry, sedimentation field flow fractionation, capillary hydrodynamic fractionation, dynamic light scattering, and differential mobility. Aggregate shape can be estimated by oil adsorption, particularly DBP, specific volume from density-pressure curves, and TEM.

Examples of morphological properties and tests used to measure them are shown in Table 1 below. These morphological values may be used alone or in combination with other morphological values.

TABLE 1

| Morphological Property | Testing Method |
| --- | --- |
| Particle size and distribution | Transition electron microscopy (TEM) Calculation from surface area Masstone |
| Surface area | Nitrogen adsorption (ASTM D 3037) Iodine adsorption (ASTM 1510) CTAB adsorption (ASTM D 3765) Carman surface area |
| Pore size and distribution | Difference between nitrogen and CTAB surface areas |
| Aggregate size and distribution | TEM Light scattering Disc centrifuge |
| Aggregate shape | TEM Oil absorption DBP absorptometry Specific volume from density-pressure curves |

The method of the present invention may further comprise the step of selecting based in part on at least one chemical value in the various embodiments of the present invention. The chemistry of a particulate material is the material's overall (or bulk) composition, surface composition, and/or extractable materials. The types, quantities, and arrangement of chemical moieties at the surface is called the surface chemistry. For example, the surface of carbon black may include carbon-oxygen surface groups, carbon-hydrogen surface groups, and/or other substituted carbon groups.

The chemical value of the particulate material can be determined using any technique known in the art. For example, the amounts of chemical moieties can be measured by desorption (for example, desorption of oxygen groups on carbon black), neutralization of surface groups by acids and bases, potentiometric, thermometric, and radiometric titrations, electrokinetic measurements, direct analysis by specific chemical reactions, polarography, infrared spectroscopy (IR), electron spin resonance (ESR), and X-ray photoelectron spectroscopy (XPS). The surface chemistry may be altered by chemical reactions or by removing extractable materials. Examples of chemical values include, but are not limited to, pH, functional group levels, and zeta potential.

It has been found that, in general, measurements of chemical components, along with measurements of morphology, are not enough to be able to effectively specify a particulate material and thereby provide greater consistency in an end-product. Particulate surfaces can contain a large number of different types of chemical species, and therefore far too many species would have to be identified and their relative positions on the surface determined in order to effectively specify the particulate material. Furthermore, while methods exist for qualitative and quantitative analysis, surface positioning is currently beyond the state of the art.

As described above, the interfacial potential property value may be any property that can be correlated to the interfacial potential of the particulate material. For purposes of the present invention, and as described in more detail below, results from tests that can be used to determine the interfacial potential, or to permit a way to assign a value to the particulate material itself or to a grade or brand of particulate material, which is affected by the interfacial potential properties of a particulate material are considered to be the interfacial potential property value in the present invention. These may be determined using a variety of techniques known in the art, including the following:

Interfacial potential by masstone. The optical density of a particulate material, such as a pigment, in a matrix depends on its intrinsic properties and how the particulate material is dispersed throughout the matrix. If poorly dispersed, then the optical density is low. If well dispersed, the optical density is high. The dispersibility of a particulate material depends on both its morphology and on its interfacial potential. Therefore the masstone depends on the interfacial potential of the pigment. The difference in masstone for the same particulate material dispersed under the same conditions in different matrices can be used as a specification for the interfacial potential of the particulate filler.

Interfacial potential by gas adsorption techniques. Some of the methods described above for determining surface area from the adsorption of gases, e.g., BET analysis, fit the data with two parameters—one for the surface area and one for the solid-gas interaction. The parameter for the solid-gas interaction is a measure of interfacial potential. Therefore from the same data that is used to report surface area by BET analysis, information about the interfacial potential is available. Therefore, a method which involves measuring the adsorption of gases other than nitrogen or krypton, which are common "inert" gases used for BET analysis, can be used for determining interfacial potential (interfacial potential vapor adsorption techniques). Examples of alternative gases which can be used for measuring interfacial potential include water, ammonia, and various organic vapors such as toluene, ethanol, pentane, nonane, acetonitrile, methylene chloride, and the like. A preferred gas adsorption technique and data analysis to obtain interfacial potentials is to measure the spreading pressure, which is described in more detail below.

Interfacial potential from adsorption from solution. Adsorption from solution is a similar technique to the adsorption of gases. Many solutes are surface active, that is, they preferentially accumulate at the surface of a particulate material when it is mixed into a solution. The amount of adsorption depends on the surface area, the morphology, and the interfacial potential. If the amount of adsorption of two or more different surface active solutes are measured on the same particulate material, then sufficient information is gathered to be sensitive independently to the morphology and interfacial potential, and would therefore be useful as a method for determining interfacial potential. For example, if the adsorption of iodine and CTAB are measured on the same carbon black at concentrations less than that required to form saturated surface layers, then sufficient information can be gathered to be sensitive independently to the morphology and interfacial potential.

Interfacial potential from light scattering or disc centrifuge. To obtain aggregate size by light scattering, a particulate material must be highly diluted into a liquid. Often a surfactant is added to insure that the particulate material is well separated and does not flocculate during the time of measurement, allowing for an accurate measure of size. A variation of this test would give information about interfacial potential, especially the cohesion of the particulate material. For this method, the particle size would be measured as a function of time with no surfactant added. A dispersion, even when highly dilute, will flocculate with time. The rate of flocculation is a measure of the cohesion of the particulate material. Therefore a measure of the particle size or the particle size distribution as a function of time is a measure of the interfacial potential, and, in particular, cohesion.

Interfacial potential by oil absorption. A common type of QA/QC test for the structure of particulate materials such as carbon black is to add a liquid slowly to a mass of material as it is being stirred. As the ratio of the volume of liquid to the mass of particulate material increases, the torque required to mix changes. Typically, the ratio of the volume of liquid added to the mass of material at the maximum torque is reported as a QA/QC test for structure and may appear on a product specification sheet. Another QA/QC test is to report the same ratio at a predetermined fraction of the maximum torque. A preferred liquid is dibutyl phthalate (DBP), and the reported value is often referred to as the DBP number. Paraffin oil has also been used. These volumes to mass ratios are strong functions of the morphology of the particulate material.

However, the flow of a particulate material wetted by a liquid also depends on the interfacial potential through the relative strengths of particle-particle interactions and particle-liquid interactions. When an absorptometer test is repeated with a second liquid on the same particulate material, the relation between torque and volume of liquid added changes. For example, maximum torque may be different for the same particulate material in different liquids, or, alternatively, the volume of liquid added to reach the maximum torque may be different. These differences reflect the interfacial potential of the particulate materials. Therefore combinations of oil absorption tests with different liquids can be used to specify the interfacial potential of a particulate material. Preferably the absorptometry method uses a liquid other than DBP or paraffin oil. Examples of liquids that can be used include propylene carbonate, water, ethylene glycol, or mixtures thereof.

Interfacial potential by wicking rates. When a particulate material is packed into a column and the bottom of the packed bed contacts a liquid, the liquid will wick up through the packed bed. The wicking rate depends on the packing of the particulate material (which depends on morphology) and the strength of interaction between the particulate material and the liquid (which depend on interfacial potential). A comparison of wicking rate for two or more liquids, which may include nonane, hexadecane, isoalkanes, ethylene glycol, formamide, bromonaphthalene, acetonitrile, benzaldehyde, propylene carbonate, aniline, cyclohexanol, nitroanisole, dichlorobenzene, water, or mixtures thereof, into equivalent packed columns of the same particulate material can be used as a measure of the interfacial potential of the particulate material. The choice of liquids is dependent on a variety of factors, including toxicity, vapor pressure, viscosity, and polarity. In general it is preferred to use liquids which have low toxicity, low vapor pressure (such as below 0.6 kPa) and/or low viscosity (such as below about 5 cp). Also, a range of polarities is preferred.

Interfacial potential by rheological tests. The degree of flocculation of a particulate material in a liquid depends on the balance between the particle-particle interactions and the particle-liquid interactions. In other words, the degree of flocculation depends on the interfacial potential of the particulate material. One measure of this balance is the degree of shear thinning—the drop in viscosity with an increase in shear rate. Another measure of the degree of flocculation is the Bingham yield point. Yet another measure of the degree of flocculation, is the elastic modulus at low strains. Each of these methods can be used for determining the interfacial potential of the particulate material. For example, a yield point method using hydrocarbon fluids such as paraffin oil, hexadecane, nonane, or mixtures thereof, may be used to determine interfacial potential.

Interfacial potential by sedimentation volumes. As dispersions flocculate, particle settling occurs because the size of the particles increases. If the particle-particle energies are strong compared to the particle-liquid energies, the flocs are large and the sediment height high. Therefore measures of the sediment height of flocculated dispersions of particulate material can be used as a measure of the interfacial potential.

Interfacial potential by phase segregations. When a particulate material is added to a container with two or more immiscible liquids, the material can preferentially accumulate in one of the phases or at the phase boundary. This preferential segregation is a consequence of the interfacial potential of the particulate material and can therefore be used as a specification for a particulate material.

Interfacial potential by inverse gas chromatography. Inverse gas chromatography (IGC) is the measurement of the retention times of gas probes flowing through packed beds of particulate materials. The stronger the interfacial potential, the longer the retention time. The retention time also depends on the morphology and packing of the particulate material. Thus, in a typical procedure, the retention times of organic vapors are compared with those of hydrocarbons. This analysis provides a measure of the interfacial potential of the particulate material and can therefore be used as a method for specifying a particulate material. Organic vapors that can be used as a measure of interfacial potential by IGC include butane, pentane, hexane, heptane, tetrahydrofuran, acetone, ethyl acetate, ether, chloroform, acetonitrile, or mixtures thereof.

Interfacial potential by spreading pressure. The spreading pressure of a gas on a particulate material is a measure of the interfacial potential. It can be calculated from the gas adsorption isotherm (moles adsorbed as a function the partial pressure of the gas). The spreading pressure is the integral under the adsorption curve when the partial pressure is plotted as a logarithm. If the data is reported as moles adsorbed per unit mass, the spreading pressure is energy per unit mass. The calculated spreading pressure can be divided by the specific surface area to give the interfacial potential in units of energy per unit area. A wide variety of gases can be used, including, for example, tetrahydrofuran, water, ethanol, toluene, methyethyl ketone, cyclohexanone, and the like. Calculating the spreading pressure of a particulate material for each gas provides a measure of the interfacial potential.

Other methods for determining the interfacial potential of the particulate material can be used and will be known to one skilled in the art. Examples include:
a) by compressing the particulate material to give a flat surface upon which the contact angle of a probe liquid can be measured;
b) by measuring the pressure of gas to remove a probe liquid from the pores of a packed bed of the particulate material after it has been filled or partly filled by the liquid;
c) by measuring the centrifugal force necessary to immerse particles of the particulate material floating on a probe liquid;
d) by measuring the two-dimensional pressure sufficient to force particles of the particulate material floating on a probe liquid in a Langmuir trough;
e) by measuring the relative adsorption of dye probes;
f) by measuring the heat when the particulate material is immersed into a probe liquid;
g) by measuring the heat released when a test adsorbate is adsorbed by the particulate material. This may be done in a flow calorimeter with the adsorbate dissolved in a carrier liquid, or in a batch calorimeter where the adsorbate is either a neat liquid or a solution.
h) by measuring the sediment volumes in an homologous series of test liquids, as described in Morrison, I. D.; Ross, S. Colloidal Dispersions: Suspensions, Emulsions, and Foams; John Wiley & Sons: New York; 2002, pp 505-515, which is incorporated in its entirety by reference herein;
i) by determining the composition of a solvent mixture just sufficient to immerse floating particles of the particulate material;
j) by measuring the deviations in viscosity from the Einstein equation for the flow of hard spheres or other deviations from the behavior of hard sphere dispersions at higher concentrations.

Another aspect of the present invention relates to an improved method for developing a particulate material that will engender superior performance when used in compositions or in matrix compounds. The invention recognizes that the interfacial potential of the particulate material as it interacts with itself and with the matrix can be important in determining performance. Other characteristics of the particulate material, such as its morphology can also be important and this invention is compatible with improving performance by controlling these other characteristics along with interfacial potential. The method has two major distinct steps. The first is to develop an understanding of how the interfacial potential affects performance. This understanding is in the form of a mapping. The second step is either to select from an existing inventory of particulate materials one or more that have interfacial potential values that will engender improved performance or to select manufacturing process conditions that will create particles with the desired interfacial potential values. Selecting the proper manufacturing conditions relies upon a second type of mapping, i.e. one that displays the relationship between manufacturing process parameters and the resulting interfacial potential.

In one embodiment of this aspect of the present invention, the performance of compositions comprising particulate materials, such as carbon black and the like, can be mapped to display how performance properties, such as electrical resistance or conductivity, impact strength, color, UV resistance, modulus, compound moisture absorption, rheology, conductivity, dispersibility, reinforcement, powder flow, tribocharging, and the like, depend upon the interfacial potential of the particulate materials. Thus, for this embodiment, the present invention relates to a performance map comprising
A) at least one performance property of a composition comprising a matrix and a particulate material, and
B) 1) at least one homogeneous interaction parameter for the particulate material or
B) 2) at least one homogeneous interaction parameter for the particulate material and at least one heterogeneous interaction parameter for the particulate material and the matrix. The interaction parameters are as described above. This mapping of performance can be done by the customer, by the particulate manufacturer and/or by any third party. The mapping, for instance, can be in the form of figures, raw data, charts, formulas, algorithms, and the like. The mapping preferably provides trends and/or functional relationships between a) the various interfacial potential values (also referred to herein as of the particulate materials and/or combinations of the interfacial potential values of the particulate materials and those of the matrix and b) at least one performance property of the composition containing the particulate materials. The interfacial potential values of a matrix or other properties of the matrix may optionally be used or determined to better understand the trends or functional relationships described herein. Generally, at least two particulate materials having different interfacial potential values are used to create a map. More preferably, at least three, at least four, at least five, or at least ten different particulate materials, and so on can be used to map performance. Preferably, each of these particulate materials has a different interfacial potential value. The interfacial potential can be measured as a single value or as two, three or more values. That is the interfacial potential can be one number or it can be two or more numbers representing different components of the potential. An example of two components is the polar and non-polar components and an example of three components is the non-polar, acid and base components.

The number of particulate materials needed to map performance may equal or exceed the number of components assigned to the interfacial potential. The particulate materials can have the same or different morphological values and/or chemical values. If the performance of the composition depends upon the morphology or other characteristics of the particulate material as well as the interfacial potential, the number of particulate materials may be increased so as to assure that the mapping is not confounded. By using a selection of particulate materials with a broad range of interfacial potentials, a broad mapping of performance properties of the composition containing the particulate materials can be obtained. This mapping can then be used to decide upon a better or improved or more appropriate particulate material or the best or most appropriate particulate material for use in the matrix to obtain the desired performance.

The mapping may be a 2-dimensional representation or may be multi-dimensional. Preferably the mapping provides trends and/or functional relationships that take into account the various interfacial potential values of the particulate materials as well as one or more properties of the matrix. The term "properties of the matrix" may include its interfacial potential values and/or other physical properties such as molecular weight, molar volume, dipole moment, relative permittivity, viscosity, density, surface tension, melting point, glass transition temperature, color, UV absorption, and the like. The properties of the matrix may be derived from published scales such as Hildebrand parameters, hydrogen bonding characteristics, electrostatic factors, fractional polarity, Hansen solubility parameters, Snyder's Polarity index, solvatochromic parameters, and the like. The properties of the matrix may be derived from one or more performance properties of the matrix once combined with at least one particulate material. The properties of the matrix may be derived from one or more performance properties of the matrix combined with each of a set of particulate materials. If the mathematical relation between the performance property of the compositions and the interfacial potential properties of both the particulate material and the matrix is known, and the values of one or more particulate materials is known, then measurements of that performance property can be interpreted to calculate the interfacial potential of the matrix. For example, the properties of a matrix may be derived from viscosities of the matrix combined with each of a set of two or more particulate materials. The properties of a set of matrixes may be derived from one or more performance properties of the matrixes combined with each of a set of particulate materials. Alternatively if the mathematical relation is known, a self consistent set of interfacial potential values of matrixes and particulate materials may be derived from one or more performance properties of each matrix combined with each particulate material. Deriving a self consistent set of interfacial potential values for both the particulate materials and the matrixes may require examining a large number of combinations.

The mapping may provide trends and/or functional relationships that also take into account one or more morphological values of the particulate materials. For example, the mapping may be between a) the various interfacial properties of the particulate material and their DBP values (and optionally take into account the properties of the matrix containing the particulate materials) and b) the conductivity of the composition containing the particulate materials. The morphological property may be the surface area or a combination of surface area and DBP value.

The mapping may be at a fixed concentration of particulate materials in the matrix or may be a mapping that can be used over a range of concentrations. For example the mapping of a performance property such as viscosity or color may account for variations in the mass fraction of particulate material added to the matrix. The mapping may account for variations in the preparation of the particulate materials in the matrix. For example, one mapping may be given for mixing the particulate materials in the matrix at high shear rates for extended times and another mapping may be given for mixing the particulate materials in the matrix with a minimum amount of stirring. Different mappings may be provided for different conditions such as temperature variations or variations in ambient conditions.

The mapping of performance property of the various interfacial potential values of particulate materials will generally be different for each matrix. A customer may be sufficiently interested in an improved performance property that the customer would use a different matrix. The mappings of performance properties of various particulate materials in various matrixes provide a method by which one or more performance properties can be improved by a choice of both a particulate material and a matrix.

Thus, in one embodiment, the present invention relates to a method to develop a new or improved product containing at least one type of particulate material by mapping the performance as described above. This mapping of performance will also permit one to identify a preferred particulate material from knowing the desired interfacial potential value or values. This mapping of performance will also permit one to identify trade-offs between interfacial potential values and morphological values and/or other values. More than one performance property may be improved simultaneously by using maps for two or more performance properties. This mapping of performance will also permit one to identify particulate materials that enable desirable trade-offs between desired performance properties. For example, maps of interfacial potential values and color and impact strength will permit one to choose a particulate material that provides satisfactory or enhanced performance in both performance properties.

By mapping performance, it may be determined that none of the particulate materials is optimal or sufficient for the desired performance. For instance, after mapping performance, there may be two particulate materials whose performances are located on either side of a more desired performance property. In such a situation, if there is no particulate material available in the manufacturer's library or inventory that fits the specific desired particulate material having the desired interfacial potential value to match the desired performance property, then the manufacturer or third party can proceed with manufacturing the particulate material having the desired interfacial potential value. Put another way, a "sweet spot" can be decided or determined by mapping performance versus interfacial potential values for various particulate materials, and once this "sweet spot" is determined, either the manufacturer can check inventory or a library of particulate materials to see if a particulate material suits this desired "sweet spot" or the manufacturer can proceed with making a particulate material that was previously not available. Alternatively a desired performance of the composition may improve as one or more values of the interfacial potential is increased or decreased. In this case a better performing composition would contain a particulate material with higher or lower interfacial potential values than any available from the manufacturer and the manufacturer could proceed to make a particulate material with higher or lower values. For purposes of the present invention, an optimal value, or optimum value, or improved value includes values that are better than one previously obtained on a consistent basis by the customer, from the standpoint of performing better with respect to at least one performance property.

The performance property can be mapped with a specific matrix, such as a customer's exact formulation or a surrogate of the customer's exact formulation, such as a chemically related formulation. The performance properties of various particulate materials in the customer's exact formulation can be executed by the manufacturer of the particulate materials or by the customer or by a third party. For example, the manufacturer of the particulate material could give a set of particulate materials of varying interfacial property values, the customer could evaluate the performance properties of those particulate materials in the customer's own matrix and a map constructed. The manufacturer can use different matrixes to find one where the map is similar to that of the customers. This map could be used to select other particulate materials to test.

The performance property can be mapped for classes of matrixes, such as various chemical categories of polymers. By mapping the performance of a particulate material in a specific customer formulation, and determining the preferred interfacial potential values, the mapping of performance will provide specific suggested particulate materials for the customer's exact formulation. However, in situations where broader knowledge is preferred or where a customer prefers not to provide an exact formulation to the particulate material manufacturer, the manufacturer, or other, can develop and provide performance mapping for broad categories of matrices or formulations such as for polyethylene, polystyrene, and other thermoplastics and the like. This more general performance mapping is ideal when a customer is developing a new product and wishes to optimize a particulate material as part of that new formulation. The general performance mapping can especially be done for standard matrices, such as standard polymers, which are generally used in various applications. For example the performance properties, such as conductivity, dispersability, or color, for various particulate materials in polystyrenes, polyacrylates, polyurethanes, polyethylenes, hydrocarbon oils, printing oils, silicone oils, silicon polymers, can be constructed and supplied as guidelines for choosing particulate materials. This type of general mapping of performance provides an excellent relationship and knowledge base for the manufacturer and customer to develop new formulations and optimize previous formulations. Also, as stated above, the mapping of performance can be done for the particulate material alone or in a matrix as described also above.

When making a particulate material having the desired interfacial potential value, one can take a previously known particulate material having a previously known interfacial potential value and study how that specific previously known particulate material was made and then, using those settings as a starting point, one can manipulate one or more various parameters to adjust the manufacturing process to manufacture the desired particulate material having the desired interfacial potential value. Process variables may include temperature, pressure, chemical composition, stoichiometry, reactor quench length, amount of quench air, feedstock composition, primary fuel type, type and/or level of downstream additives, or type, concentration, and/or amount of post treatment. For instance, one can adjust any one or more of the following parameters: ratio of air to fuel; percent secondary air; percent downstream air; quench levels and/or length of quench; staged introduction of fuel or feedstock; percent oxygen; dryer temperature; percent oxygen in dryer; feedstock and use of secondary gas; and feedstock and use of atomization, and the like. Other examples include air preheat to the primary burner, air/gas ratio in the primary burner, ratio of total air to total feedstock, potassium consumption, feedstock quality (including feedstocks comprising natural gas), type of gas or oil in the primary burner, atomization of the quench, quench water quality, type of pelletization (such as wet or dry pelletization), type and amount of additives (such as additives introduced in the gas stream, additives introduced as gases before the quench, and additives added in the pelletizer), type and level of gases introduced in the dryer, and temperature and pressure (particularly in a dryer). Thus, process variables which effect conditions under which the particles are formed may be adjusted, as well as conditions for post treatment. Examples of post treatment include chemical modification of the particulate material (such as surface reactions and chemical attachments) as well as the use of adherents (such as surfactants and dispersants).

In another embodiment of the present invention, the process variables described above in making various particulate materials having different interfacial potential values can be mapped with respect to the interfacial potential value achieved. Thus, this type of mapping of process variables will permit one to achieve readily a desired interfacial potential value by knowing which process variable to change in order to achieve the desired interfacial value for a particulate material. Furthermore, this mapping of process variables will permit one to improve manufacturing processes by choosing conditions or combinations of conditions that attain the desired interfacial potential values while simultaneously improve manufacturability, capital equipment requirements, or yield, or cost or combinations.

The present invention will be further clarified by the following examples which are intended to be only exemplary in nature.

EXAMPLES

Example 1

Standard grades of carbon black are available from various manufacturers. One of the Q/C specifications for these standard grades is the DBP number. The volume at maximum torque for dibutyl phthalate (DBP) is a QA/QC measure of the morphology of the carbon black.

The DBP value was measured on six standard grades in a Brabender mixer with a device having a means for recording the torque data. The data is reported in the Table 2 below. The carbon blacks are ordered by their DBP numbers.

Determining the volume at maximum torque for another liquid is an example of a QA/QC test for the interfacial potential of the carbon black, which may be used to specify the particulate material. For this example, water, a 60/40 ethylene glycol/water mixture (60 parts ethylene glycol by volume to 40 parts water by volume), ethylene glycol, and paraffin oil were used. The volumes at maximum torque are also shown in Table 2. These results show that standard grades order differently depending on which liquid is used as a probe liquid. For example, looking at the data for water, as the DBP number increases, the interfacial potential property value may increase or decrease. When these carbon blacks are used in applications where both structure and interfacial potential are the significant factors, the product properties may therefore vary unexpectedly. Therefore, at least one interfacial potential property value would be included in order to specify these particulate materials, particularly on a product specification sheet.

TABLE 2

| Sample name | Volume @Max T for 5 liquids | | | | |
|---|---|---|---|---|---|
| | Water | 60% glycol | 100% glycol | DBP | Paraffin Oil |
| ASTM Reference Black A6 | 205.5 | 152.6 | 128.3 | 128.7 | 130.65 |
| ASTM Reference Black B6 | 238 | 142.3 | 119.5 | 121.7 | 123.75 |
| ASTM Reference Black C6 | 154.55 | 94.6 | 74.9 | 80.4 | 83.05 |
| ASTM Reference Black D6 | 122.2 | 81.5 | 69.8 | 74.05 | 75.9 |
| ASTM Reference Black E6 | 150.8 | 103.3 | 88.9 | 95.25 | 98.1 |
| ASTM Reference Black F6 | 227.3 | 156.2 | 133.9 | 137.9 | 139.6 |

Example 2

Manufacturers often produce the same product at different manufacturing plants. The products need to meet the product specifications regardless of where they are produced.

Table 3 shows data taken on the same grade of carbon black from four manufacturing plants. In this example the "% of max DBP" is the percentage of the maximum DBP value in the table, which was that of Plant E. The DBP numbers were measured as the volume at maximum torque on a Brabender abosrptometer with a device capable of recording the torque data. Note that the DBP values are nearly identical (within approximately 96% of the maximum value). The DBP values are part of the current product specification and by this criterion, all the samples would therefore be considered to be the same (i.e., within spec).

The volume at maximum torque was also measured for three other liquids: ethylene glycol (EG), 60/40 ethylene glycol/water (60 parts ethylene glycol by volume and 40 parts water by volume), and pure water. This is an example of an interfacial potential property test.

TABLE 3

| Sample name | Volume @Max Torque | | | |
|---|---|---|---|---|
| | % of max DBP | EG | 60% EG | Water |
| Plant A | 97 | 77.1 | 108.8 | 17.15 |
| Plant B | 98.8 | 71.95 | 92.9 | 132.15 |
| Plant C | 97.8 | 72.8 | 90 | 138.35 |

TABLE 3-continued

| Sample name | Volume @Max Torque | | | |
|---|---|---|---|---|
| | % of max DBP | EG | 60% EG | Water |
| Plant D | 95.8 | 82.3 | 115.4 | 145.8 |
| Plant E | 100 | 73.5 | 91.9 | 100.35 |

As the data in Table 3 shows, the volumes obtained for the other liquids are not the same from manufacturing plant to manufacturing plant. This means that the interfacial potentials are not the same for the four samples and hence the products are not the same. Thus, the products would be better specified if at least one of these interfacial potential property values were included.

Example 3

The carbon black of Example 2 had a low DBP value. A similar test was done for a grade of carbon black with a higher DBP specification. Samples were taken from three manufacturing plants. Again the volume at maximum torque with DBP was measured in a Brabender absorptometer with a device having a means of recording the torque data, and the results are shown as a percentage of the maximum value (Plant F). Results are shown in Table 4 below. The volume at maximum torque was also measured with ethylene glycol (EG), 60/40 EG/water (60 parts ethylene glycol by volume and 40 parts water by volume), and pure water, and the resulting data are also shown in Table 4.

TABLE 4

| Sample name | Volume @Max Torque | | | |
|---|---|---|---|---|
| | % of max DBP | EG | 60% EG | Water |
| Plant F | 100 | 115.3 | 150.5 | 217.1 |
| Plant G | 98.3 | 114.0 | 141.5 | 183.95 |
| Plant H | 97.2 | 111.5 | 138.9 | 208.2 |
| Plant I | 97.5 | 114.1 | 139.6 | 226.75 |

The data shows that when an interfacial potential property value is measured, the grades made in different plants are found to be different. Thus, inclusion of at least one interfacial potential property value would be useful in specifying these particulate materials.

Example 4

Modern carbon black manufacturing plants can be run under a variety of process conditions and still produce product that has nearly the same standard QA/QC values (Analytical Properties), such as iodine numbers (I2 Number), DBP number (DBPA), nitrogen surface area (N2SA), t-area (STSA), and tint. The upper rows in the Table 5 below shows that by the standard QA/QC values, the listed carbon blacks are the same. However, when the interfacial potentials are measured by the rate of wicking of various liquids up a packed powder bed, using the Bartell method (which is described in Morrison, I. D.; Ross, S. Colloidal Dispersions: Suspensions, Emulsions, and Foams: John Wiley & Sons: New York; 2002; pp 210-212, incorporated in its entirety by reference herein), significant differences can be seen. The wicking rates have units of $g^2/s$.

TABLE 5

| | Analytical Properties | | | | | | | | | | |
|---|---|---|---|---|---|---|---|---|---|---|---|
| I2 Number | 71 | 85.3 | 88 | 86.5 | 88.6 | 85.7 | 85.8 | 85.8 | 82.2 | 85.9 | 87.9 |
| DBPA | 108 | 106.9 | 108.2 | 106.5 | 108.1 | 104.9 | 104.4 | 105.9 | 104.5 | 102.9 | 107.8 |
| N2SA | 61.8 | 75.6 | 76 | 75.7 | 75.7 | 73.9 | | 76.1 | 73.6 | 74.6 | 77 |
| STSA | 61.4 | 74.7 | 71.7 | 72.2 | 69.6 | 69.4 | | 72.8 | 70.3 | 70.1 | 71.3 |
| Tint | 89.3 | 105.5 | 99.2 | 98 | 99.3 | 104 | 98.1 | 94.1 | 98.3 | 102.9 | 94.8 |
| | Wicking Rates | | | | | | | | | | |
| Water | 0.0005 | 0.0011 | 0.0011 | 0.0007 | 0.0009 | 0.0006 | 0.0007 | 0.0006 | 0.0006 | 0.0009 | 0.0010 |
| Formamide | 0.0044 | 0.0062 | 0.0049 | 0.0039 | 0.0063 | 0.0049 | 0.0054 | 0.0029 | 0.0025 | 0.0045 | 0.0050 |
| Ethylene Glycol | 0.0023 | 0.0011 | 0.0012 | 0.0008 | 0.0016 | 0.0011 | 0.0016 | 0.0007 | 0.0004 | 0.0012 | 0.0015 |
| Bromo-naphthalene | 0.0060 | 0.0023 | 0.0031 | 0.0017 | 0.0021 | 0.0017 | 0.0017 | 0.0017 | 0.0011 | 0.0020 | 0.0020 |
| Pentane | 0.0212 | 0.0046 | 0.0077 | 0.0029 | 0.0074 | 0.0091 | 0.0070 | 0.0038 | 0.0028 | 0.0049 | 0.0085 |
| Tetrahydrofuran | 0.0094 | 0.0055 | 0.0125 | 0.0047 | 0.0185 | 0.0065 | 0.0138 | 0.0062 | 0.0032 | 0.0090 | 0.0136 |

Thus, while these particulate materials are all the same by the standard specification, they differ by their interfacial potentials, and the method of the present invention, which comprises assigning at least one interfacial potential property value, would be able to distinguish between them.

Example 5

The previous examples have used a single interfacial potential parameter from each test. However combinations of multiple parameters can also be used.

An absorptometer (available from C. W. Brabender Instruments, Inc., 50 E. Wesley St., South Hackensack, N.J. 07606) was used following the procedure described in ASTM test D-2414-01. Dibutyl phthalate (DBP) was added by means of a constant-rate buret to a sample of carbon black in the mixer chamber. A torque sensor detected the rise in viscosity from the free-flowing powder to the semi-plastic flow of the continuous mass. The absorptometer and buret were shut off when the torque passed through its characteristic maximum in such a fashion that there was assurance that the maximum torque had been reached. The volume of DBP per unit mass of carbon black was recorded as the DBP absorption number. CDBP values were obtained using a similar test in which the carbon black was pre-compressed before conducting the test. (ASTM D-3493)

This data is shown in Table 6, along with the iodine number and nitrogen, and STSA surface area values. These morphological values are reported as a percentage of the maximum values in the table. Note that, based on all of the values shown and, in particular, the values for the standard liquid DBP, these materials would be considered identical.

TABLE 6

| Sample | % of max DBP number (cc/100 g) @70% | % of max CDBP (cc/100 g) @70% | % of max I₂No (mg/g) | % of max BET surface area (m²/g) | % of max STSA (m²/g) |
|---|---|---|---|---|---|
| CB-A | 100 | 100 | 91.1 | 97.6 | 95.1 |
| CB-B | 99.2 | 96.4 | 95.6 | 95.1 | 92.7 |
| CB-C | 98.3 | 96.3 | 95.6 | 97.6 | 97.6 |
| CB-D | 99.2 | 94.0 | 97.8 | 100 | 100 |
| CB-E | 98.3 | 100 | 100 | 100 | 97.6 |

A similar absorptometry procedure was followed, using paraffin oil, ethylene glycol, water, and a 60/40 mixture of ethylene glycol and water. Results are show in FIG. 1. As can be seen, the values for the measured parameters in ethylene glycol are different for each sample. The same is true for the paraffin oil. Significant separations between the morphologically identical samples of carbon black are found when a 60/40 ethylene glycol/water mixture (60 parts ethylene glycol by volume and 40 parts water by volume) or just pure water is used. In addition, the ordering of the samples (the carbon black samples that represent the high and low values are shown in FIG. 1) changes depending on the solvent used. Thus, FIG. 1 shows that samples of carbon black that were the same by standard morphology tests are shown to be different from each other when tested using different liquids. Therefore, these values can be used to specify the carbon black. Combinations of these values may also be used. Inclusion of the morphological values would provide for even better product specification.

Figure 2:
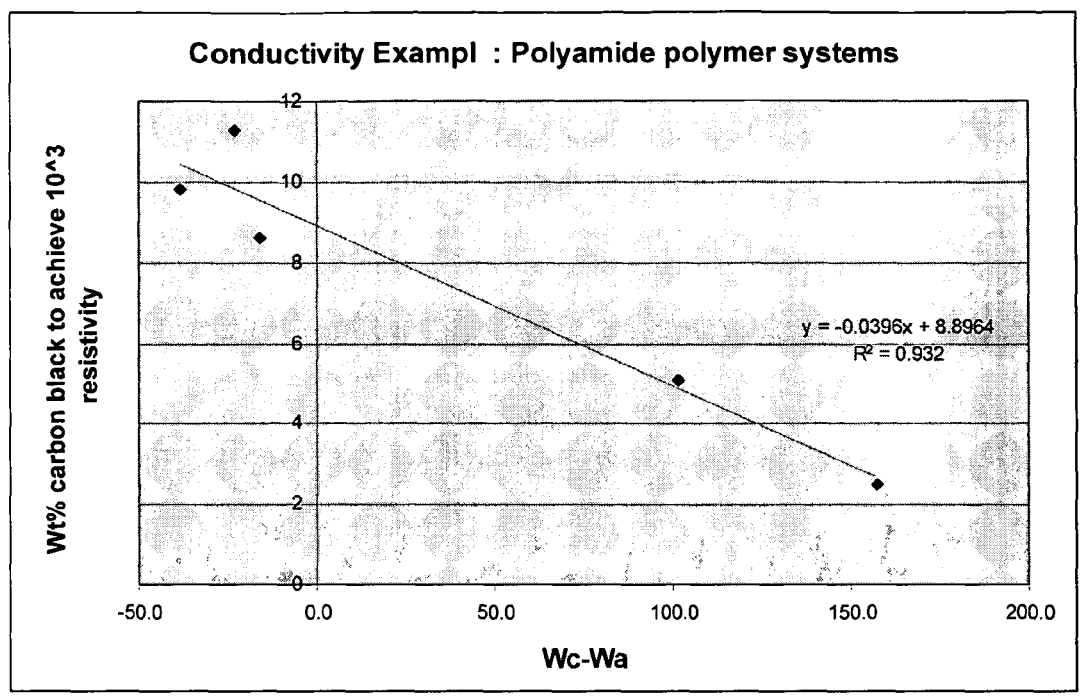

FIGS. 1 and 2 illustrate the utility of calculating the work of cohesion (Wc) and work of adhesion (Wa) for high-density polyethylene and polyamide polymer systems with respect to interfacial property values of carbon black particles and the matrix. Using a predetermined relationship between conductivity and carbon black loading, a combination of interfacial properties can be used to predict the quantity of carbon black required achieving a specific resistivity of the composite. For example, to attain a conductivity of 10^3 ohms/cm using 5% carbon in the composite, the Wc-Wa value must be approximately 200. Increasing the carbon black loading requires reducing the magnitude of the Wc-Wa value to maintain the set composite resistivity. This type of plot is particularly useful when the carbon black particles serve more than one function. For example, cable coating may require a specific conductivity and UV stability. Increasing the carbon black loading to improve the UV resistive characteristics would also increase the conductivity in an undesirable manner. Therefore, a specific carbon black particle could be chosen using the information in FIGS. 1 and 2 meet UV and Conductivity specifications.

Figure 3:
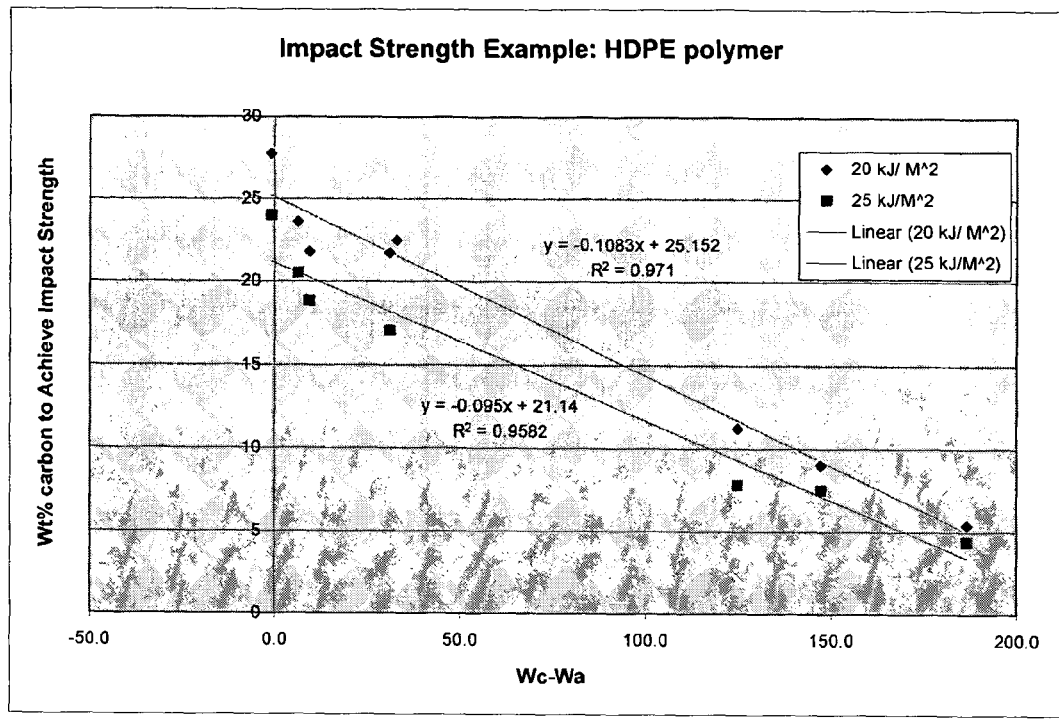
Figure 4:
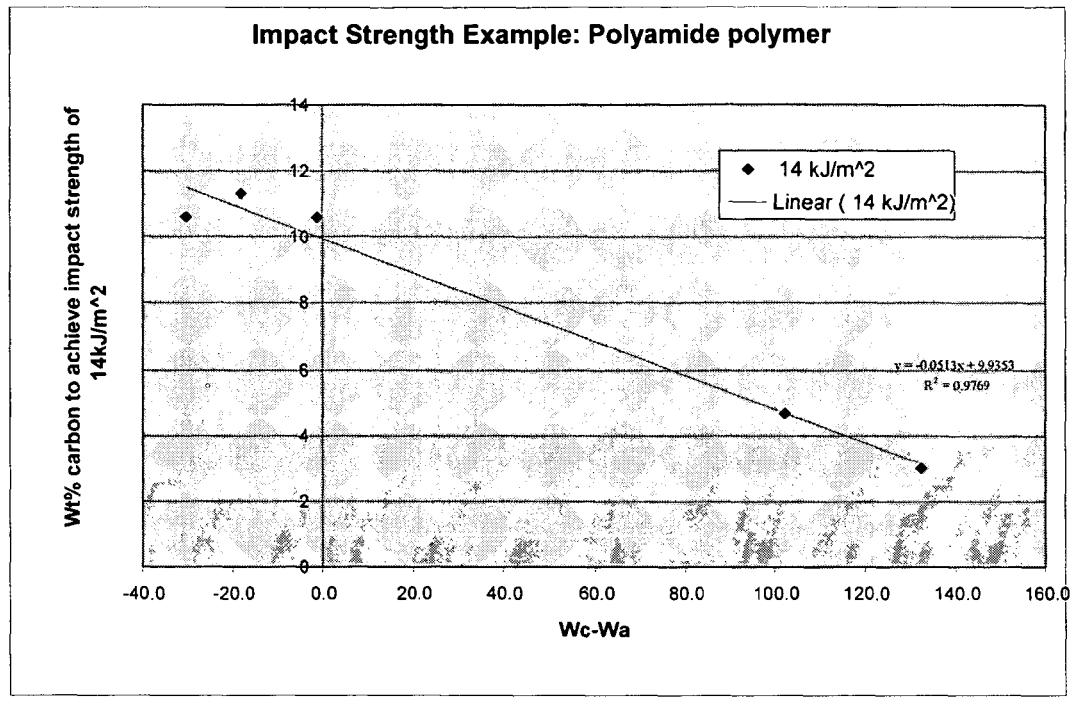

FIGS. 3 and 4 further illustrate the utility of using interfacial potential values to select a carbon black for a given application. The predetermined relationships represented in FIGS. 3 and 4 for high-density polyethylene and polyamide, respectively, allow selection of a carbon black based on its interfacial properties to achieve desired impact strength. The relationship in FIG. 3, for example, indicates that a carbon black particle must have a high Wc-Wa value to achieve impact strength at 25 kJ/m2 at low carbon loadings at approximately 5 percent. Likewise a similar relationship exists for polyamide polymers as shown in FIG. 4. These types of plots indicate how to manipulate the interfacial properties of the carbon black to allow different loadings in the composite systems with out compromising the impact properties.

Example 6

The following example illustrates the utility of using interfacial potential values to determine the work of adhesion (Wa) to select an improved carbon black for dispersion in composites. A high color carbon black was tested for color and dispersion quality (i.e. smoothness) in a sytrene-arcylonitrile based polymer system. The interfacial potential values of the carbon black were determined as cited in the "*General Description of Steps to Establish Interfacial Potential Relationships*" below. The sample was further thermally treated at an elevated temperature (greater than 500 C) for a predetermined amount of time. Subsequently the sample was evaluated in the sytrene-arcylonitrile based polymer and the interfacial potential values determined. The following table summarizes the color quality in terms of L*, a* and b*, and the smoothness index with respect to Wa

TABLE 7

Example of using Wa to select carbon black particles for improved dispersion in polymer applications.

| Sample | L* | a* | b* | Smoothness index | Wa |
|---|---|---|---|---|---|
| Black A | 4.136 | −0.212 | −1.28 | 2444 | 55.8 |
| Modified Black A | 3.562 | −0.243 | −1.147 | 1822 | 72.6 |

The example shows that increasing the Wa between the matrix and the carbon black based on interfacial potential values improves color development and smoothness upon dispersion in the sytrene-arcylonitrile based polymer system. This allows a method of selecting the optimal carbon black for improved properties.

Example 7

General Description of Steps to Establish Interfacial Potential Relationships This example outlines a general method to determine the interfacial potential values of carbon black and construction of a general performance relationship or map. The steps cited are provide to establish a general mode to establish a performance relationship based on interfacial potential values and is not intended to be limited to any one particular technique.

1. Measure Wicking Rates of 15 different probes for each Carbon Black (5-7 blacks total in examples cited in FIGS. 1-4)
2. Relate wicking rates of each solid/liquid interaction to a known scale (Hansen Solubility Parameters) and Calculate the Interfacial Potential Components of each black with respect to the known liquid scale using an existing mathematical relationship. (This is in a analogous manner cited in the above referenced U.S. Provisional Patent Applications)
3. Determine interfacial properties of matrix/media contacting carbon black using known scales of interfacial potential values
4. Calculate particle—media interaction from known matrix interfacial potential values and calculated carbon black interfacial potential values. This is determines the work of adhesion between the carbon black particle and the application matrix.
5. Measure the yield point of each carbon black in mineral oil at a constant volume fraction.
6. Calculate the Particle—Particle interaction based on known carbon black physicals (surface area, density, aggregate size) This determines the Work of Cohesion of the carbon black particle with each other.
7. Determine the functional form of Wc and Wa with known performance properties, such as conductivity or impact strength, as illustrated in the provided examples, to determine the optimal properties/characteristic required for the carbon black particle

Example 8

Determination of Interfacial Property Values based on the Hansen Solubility Parameter Scale. Interfacial potential values based on the Hansen Solubility Parameter Scale were determined for carbon blacks used in plastic compositions. The wicking rates (mass$^2$/time) of eleven liquids: hexadecane, nonane, acteonitrile, aniline, benzaldehyde, cyclohexanol, o-dichlorobenzene, ethylene glycol, formamide, o-nitroanisole, and propylene carbonate, were measured on packed beds of each of seven carbon blacks. Each carbon black was packed to the same density for all test liquids. The wicking rate data and the cell dimensions are given in Table 8.

TABLE 8

Wicking Rates (g$^2$/s) and dimensions of cells

| | Sample | | | | | | | | | |
|---|---|---|---|---|---|---|---|---|---|---|
| | 568 | 561 | 560 | 481 | 562 | 467 | 555 | 502 | 502 | 505 |
| Mass (g) | 0.5570 | 1.3752 | 1.0802 | 1.1315 | 1.3206 | 0.4318 | 0.4253 | 1.1192 | 1.2883 | 1.1183 |
| Volume (cm$^3$) | 1.859 | 1.757 | 1.661 | 1.88 | 1.978 | 1.664 | 1.859 | 1.781 | 2.05 | 1.664 |
| Length (mm) | 23.04 | 14.86 | 15.4 | 16.91 | 17.94 | 14.81 | 23.04 | 15.78 | 18.14 | 14.81 |
| Area (m$^2$/gm) | 1.64E+03 | 3.58E+01 | 5.67E+01 | 2.29E+02 | 6.41E+01 | 9.45E+02 | 1.35E+03 | 5.21E+01 | 5.21E+01 | 1.17E+02 |
| Hexadecane | 6.31E−05 | 1.53E−04 | 1.75E−04 | 1.24E−04 | 1.32E−04 | 1.74E−04 | 7.34E−05 | 1.35E−04 | | 1.27E−04 |
| Nonane | 2.38E−04 | 4.95E−04 | 6.12E−04 | 4.36E−04 | 4.35E−04 | 6.22E−04 | 2.47E−04 | 5.13E−04 | | 4.31E−04 |
| Acetonitrile | 1.15E−04 | 1.58E−04 | 1.85E−03 | 1.57E−03 | 9.07E−04 | 1.37E−03 | 9.01E−04 | 1.44E−03 | | 1.30E−03 |
| Benzaldehyde | 1.15E−04 | 5.66E−04 | 8.85E−04 | 8.51E−04 | 5.87E−04 | 8.74E−04 | 3.47E−04 | | 6.29E−04 | 7.19E−04 |
| Bromonaphthalene | 1.15E−04 | 3.29E−04 | 3.72E−04 | 5.32E−04 | 3.69E−04 | 3.73E−04 | 1.87E−04 | 3.38E−04 | | 2.87E−04 |
| Cyclohexanol | 1.68E−05 | 1.79E−05 | 2.02E−05 | 1.80E−05 | 2.32E−05 | 2.55E−05 | 4.21E−05 | | 1.73E−05 | 1.75E−05 |
| Dichlorobenzene | 3.45E−04 | 1.06E−03 | 1.22E−03 | 1.16E−03 | 1.06E−03 | 1.47E−03 | 5.01E−04 | | 1.14E−03 | 9.99E−04 |
| Ethylene Glycol | 5.62E−05 | 7.93E−05 | 9.37E−05 | 1.12E−04 | 1.41E−04 | 9.91E−05 | 8.76E−05 | | 1.01E−04 | 8.11E−05 |

TABLE 8-continued

Wicking Rates (g²/s) and dimensions of cells

| | Sample | | | | | | | | | |
|---|---|---|---|---|---|---|---|---|---|---|
| | 568 | 561 | 560 | 481 | 562 | 467 | 555 | 502 | 502 | 505 |
| Formamide | 3.40E−04 | 3.80E−04 | 4.33E−04 | 6.06E−04 | 4.90E−04 | 6.31E−04 | 3.12E−04 | 4.32E−04 | | 3.73E−04 |
| Nitroanisole | 9.95E−05 | 2.54E−04 | 3.25E−04 | 4.06E−04 | 2.84E−04 | 3.32E−04 | 1.96E−04 | | 2.75E−04 | 2.49E−04 |
| Propylene Carbonate | 3.81E−04 | 5.06E−04 | 7.98E−04 | 6.64E−04 | 4.74E−04 | 6.75E−04 | 4.72E−04 | | 7.61E−04 | 6.60E−04 |

The work of adhesion between the liquid and the powder, $W_{lp}^{adh}$, was calculated for each wicking rate from the Washburn equation in the form:

$$\frac{m^2}{t} = \frac{(V_c - m_p/\rho_p)^3}{m_p \Sigma L_c^2} \frac{\rho_l^2}{\eta}(W_{lp}^{adh} - \sigma_l) \quad [1]$$

where $m/t^2$ is the wicking rate, $V_c$ is the volume of the packed bed, $m_p$ is the mass of particles in the packed bed, $\rho_p$ is the density of the particles, $\Sigma$ is the specific surface area of the powder, $L_c$ is the length of the column, $\rho_l$ is the density of the liquid, $\eta$ is the viscosity of the liquid, and $\sigma_l$ is the surface tension of the liquid.

Hansen solubility parameters are used in the plastics industry to predict the compatibility of plastics with each other and their solubilities in various solvents. The Hansen solubility parameters for the wicking liquids are given in Table 9.

TABLE 9

Hansen Solubility Parameters for Liquids

| Solvent | $S^d$ | $S^p$ | $S^H$ |
|---|---|---|---|
| Hexadecane | 16.3 | 0 | 0 |
| Nonane | 15.7 | 0 | 0 |
| Acetonitrile | 15.3 | 18 | 6.1 |
| Benzaldehyde | 19.4 | 7.4 | 5.3 |
| Bromonapthalene | 20.3 | 3.1 | 4.1 |
| Cyclohexanol | 17.4 | 4.1 | 13. |
| o-Dichlorobenzene | 19.2 | 6.3 | 3.3 |
| Ethylene glycol | 17 | 11 | 26 |
| Formamide | 17.2 | 26. | 19 |
| o-Nitroanisole | 19.1 | 9.4 | 6.1 |
| Propylene | 20 | 18 | 4.1 |

The work of adhesion is a measure of the compatibility of a powder with a matrix. The work of adhesion between a solid and a liquid may be calculated from the Hansen solubility parameters with the following equation:

$$W_{lp}^{adh} = (S_p^d \cdot S_l^d)^{1/2} + (S_p^p \cdot S_l^p)^{1/2} + (S_p^H \cdot S_l^H)^{1/2} \quad [2]$$

Where $S_p^d$, $S_p^p$, and $S_p^H$ are the corresponding Hansen parameters for the powder. These sets of three constants are interfacial potential values for the powder. A set of interfacial potential values corresponding to the Hansen Solubility Scale for each carbon black was found by a least squares fit of the measured works of adhesion and the known solubility parameters for the liquids. The results are shown in Table 10. Note that the interfacial potential values for each powder has three components.

TABLE 10

Interfacial Potential Values - Hansen Solubility Parameter Scale

| Sample Number | $S^d$ | $S^p$ | $S^H$ |
|---|---|---|---|
| 568 | 159 | 0.001 | 173 |
| 561 | 54 | 1.6 | 23 |
| 560 | 63 | 1.8 | 25 |
| 481 | 109 | 4.0 | 109 |
| 562 | 57 | 0 | 56 |
| 467 | 128 | 0.006 | 97 |
| 555 | 116 | 1.1 | 130 |
| 502 | 51 | 1.1 | 28 |
| 505 | 78 | 0.69 | 47 |

Example 9

Determination of Interfacial Potential Values on the Hildebrand Scale. Interfacial potential values based on Hildebrand Parameters were also determined for the same seven commercial carbon blocks used in plastic formulations described in Example 7. The Hildebrand parameters for nine of the liquids used in Example 8 are given in Table 11.

TABLE 11

Hildebrand Parameters for Liquids

| Solvent | $\delta_l$ |
|---|---|
| Nonane | 15.6 |
| Acetonitrile | 24.3 |
| Benzaldehyde | 21.1 |
| Bromonapthalene | 19.2 |
| Cyclohexanol | 21.7 |
| o-Dichlorobenzene | 20.5 |
| Ethylene glycol | 29.9 |
| Formamide | 39.3 |
| Propylene | 27.2 |

Hildebrand parameters are only used in the plastics industry to predict the compatibility of plastics with each other and their solubilities in various solvents. The work of adhesion between a solid and a liquid may be calculated from Hildebrand parameters by the following equation:

$$W_{pl}^{adh} = (\delta_p g \delta_l)^{1/2} \quad [3]$$

where $\delta_p$ and $\delta_l$ are the Hildebrand Parameters for the powder and the liquid respectively.

Interfacial potential values corresponding to the Hildebrand Parameter Scale for each carbon black was found by a least squares fit of the measured works of adhesion and the known Hildebrand Parameters for the liquids. The results are shown in Table 11. Note that the interfacial potential value for each powder has one component.

TABLE 11

Interfacial Potential Values - Hildebrand Parameters

| Sample | $\delta_p$ |
|---|---|
| 568 | 341 |
| 561 | 93 |
| 560 | 107 |
| 481 | 248 |
| 562 | 113 |
| 467 | 231 |
| 555 | 244 |
| 502 | 94 |
| 505 | 142 |

Example 10

Determination of Interfacial Potential Values based on an Ab Initio Scale: The work of adhesion can also be based on an independent set of parameters for the liquid as well as the powder. The equation used here is similar to Equation [2] with three parameters for each liquid and black:

$$W_{lp}^{adh} + 2(S_p^1 \cdot S_l^1)^{1/2} + 2(S_p^2 \cdot S_l^2)^{1/2} = 2(S_p^3 \cdot S_l^3)^{1/2}$$

where $S_p^1$, $S_p^2$ and $S_p^3$ are the three parameters for the powder and $S_l^1$, $S_l^2$ and $S_l^3$ are the three parameters for each liquid. These parameters can be found by minimizing the sum of squares over the entire set of data. This was done for the carbon blacks and liquids in Table 12. The liquid parameters were chosen such that the sum of parameters was equal to the liquid surface tension.

$$\sigma_l = S_l^1 + S_l^2 + S_l^3$$

The second and third component for both nonane and hexdecane were taken to be zero. The resulting parameters for the carbon blacks are given in Table 12. The corresponding values for the liquids are given in Table 13.

TABLE 12

Interfacial potential values - Ab Initio Scale

| Sample | $S^1$ | $S^2$ | $S^3$ |
|---|---|---|---|
| 568 | 49.0 | 175.0 | 4.7 |
| 561 | 10.4 | 7.1 | 8.0 |
| 560 | 12.2 | 7.8 | 9.1 |
| 481 | 23.3 | 22.4 | 24.9 |
| 562 | 11.1 | 12.7 | 8.4 |
| 467 | 25.9 | 22.6 | 14.9 |
| 555 | 24.1 | 136.2 | 16.1 |
| 502 | 10.2 | 7.0 | 7.7 |
| 505 | 16.1 | 12.4 | 11.5 |

TABLE 13

Solvent parameters - Ab Initio Scale

| Solvent | $S^1$ | $S^2$ | $S^3$ |
|---|---|---|---|
| Hexadecane | 27.1 | 0.0 | 0.0 |
| Nonane | 22.4 | 0.0 | 0.0 |
| Acetonitrile | 1.0 | 0.0 | 27.2 |
| Benzaldehyde | 4.4 | 0.0 | 34.8 |
| Bromonapthalene | 3.5 | 0.3 | 40.8 |
| Cyclohexanol | 4.5 | 29.5 | 0.0 |
| Ethylene Glycol | 4.5 | 23.7 | 19.8 |
| Formamide | 49.3 | 3.1 | 5.8 |

TABLE 13-continued

Solvent parameters - Ab Initio Scale

| Solvent | $S^1$ | $S^2$ | $S^3$ |
|---|---|---|---|
| o-Nitroanisole | 4.5 | 1.9 | 39.6 |
| Propylene | 39.0 | 1.4 | 1.0 |

Example 11

The following is an example of how a process variable can be adjusted to produce carbon blacks with similar morphological values but different interfacial potential property values Three carbon blacks (CB-6A, CB-6B, and CB-6C) were prepared using a furnace reactor similar to that shown in U.S. Pat. No. 5,456,750. Specific reactor conditions are shown in Table 14 below:

TABLE 14

| Condition | CB-6A | CB-6B | CB-6C |
|---|---|---|---|
| Burner Air Rate (nm$^3$/h) | 5976 | 5976 | 5976 |
| Burner Gas Rate (nm$^3$/h) | 305 | 305 | 305 |
| Feedstock Rate to Reactor (kg/h) | 2209 | 2225 | 2207 |
| Tangential Air to Reactor (nm$^3$/h) | 724 | 724 | 724 |
| Air Preheat (° C.) | 510 | 510 | 510 |
| Feedstock Preheat (° C.) | 173 | 173 | 173 |
| K$^+$ concentration in feedstock (gm/1000 kg) | 8.1 | 7.5 | 2.8 |
| Reactor Quench Length (ft) | 17 | 22.5 | 33.5 |

As can be seen, for these carbon blacks, the reactor inputs were kept similar while the quench length was increased from 17 ft. to 33.5 ft. In addition, the potassium concentration in the feedstock was reduced as the quench length was increased in order to maintain similar DBPA values. Table 15 shows both the morphological values (surface area and structure) as well as the interfacial potential property values (wicking rates of two liquids—ethylene glycol and bromonaphthalene, gm$^2$/sec) for each carbon black. Also included is the ratio of the two measured wicking rates.

TABLE 15

| Properties | CB-6A | CB-6B | CB-6C |
|---|---|---|---|
| Fluffy Black N$_2$ surface area (m$^2$/gm) | 76 | 74 | 76 |
| Fluffy Black DBPA (cc/100 gm) | 107 | 107 | 108 |
| Ethylene Glycol | 0.00142 | 0.00119 | 0.00150 |
| Bromonaphthlalene | 0.00162 | 0.00129 | 0.00143 |
| Ethylene glycol/Bromonaphthalene | 0.874 | 0.921 | 1.046 |

As can be seen, both the nitrogen surface area and the DBPA values for the three carbon blacks were very similar. Thus, using only these measures, the three carbon blacks would be considered similar. However, using measures of interfacial potential, it is clear that these carbon blacks are quite different.

Figure 5:
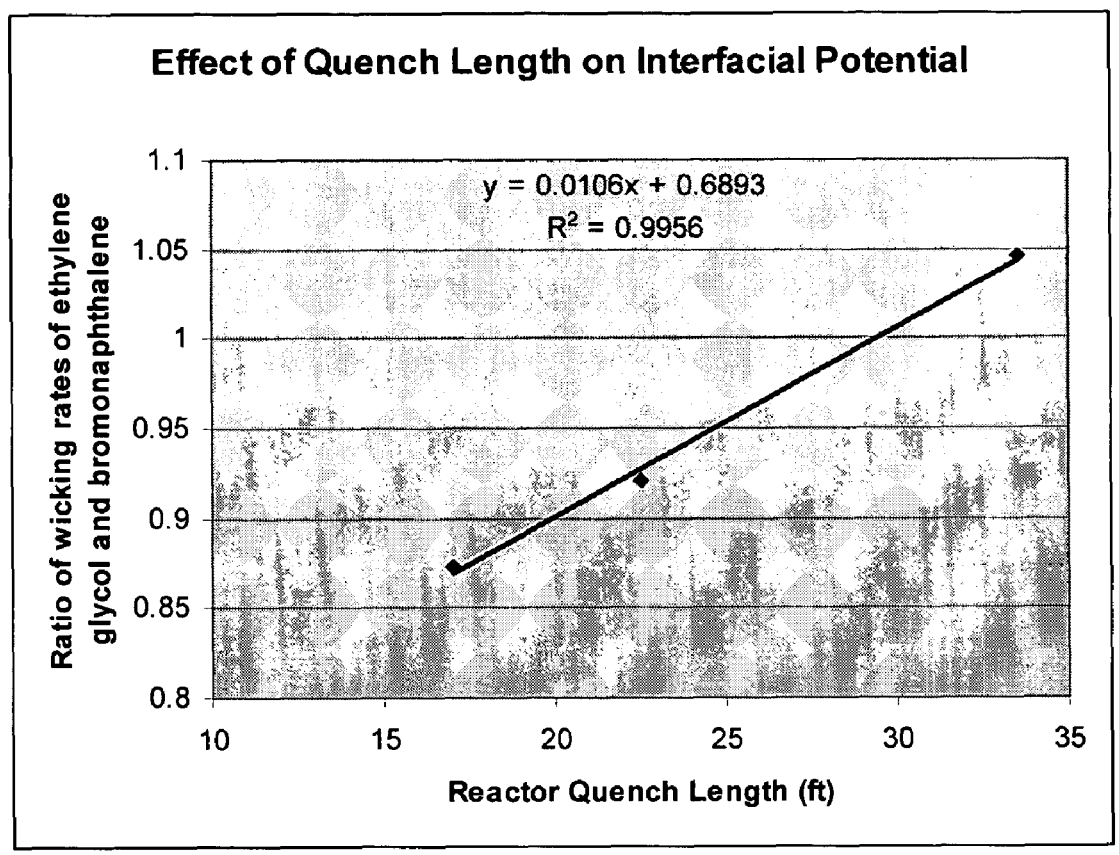
FIG. 5 is a graph showing the effect of quench length on interfacial potential values of particulate materials.

The effect of quench length on the ratio of wicking rates shown in Table 15 is shown in FIG. 5. This figure demonstrates a relationship between the process variable and interfacial potential property values.

Example 12

The following example shows the relationship between interfacial potential property values as measured by absorptometry and scorch for rubber compositions comprising a rubber and carbon black.

Table 16 lists the analytical values of five different samples of carbon black made under slightly different conditions. The table also lists the maximum torque and the volume of propylene carbonate at that torque developed in an absorptometer using a method similar to that described in Example 5. The table also lists the scorch values of each of the five blacks. Scorch value were determined using the method described in ASTM D-1646.

TABLE 16

| ID | SBR Scorch T5 | Iodine Number (mg/g) | DBP (cc/100 g) @70% | BET Surface Area (m2/g) | STSA (m2/g) | Median Aggregate Size (nm) by DCP | Delta D50 Aggregate Size (nm) by DCP | Vol at Max T Propylene Carbonate | Max T Propylene Carbonate |
|---|---|---|---|---|---|---|---|---|---|
| CB-1 | 14.8 | 84 | 74 | 77 | 76 | 87 | 62 | 88.2 | 6372.5 |
| CB-2 | 13.4 | 80 | 75 | 77 | 76 | 86 | 64 | 78.75 | 8561 |
| CB-3 | 14.5 | 80 | 75 | 75 | 75 | 85 | 57 | 77.1 | 8264.5 |
| CB-4 | 14.1 | 80 | 74 | 74 | 73 | 90 | 66 | 91.35 | 5759.5 |
| CB-5 | 16.5 | 77 | 75 | 74 | 73 | 91 | 71 | 81.55 | 5931.5 |

Figure 6:
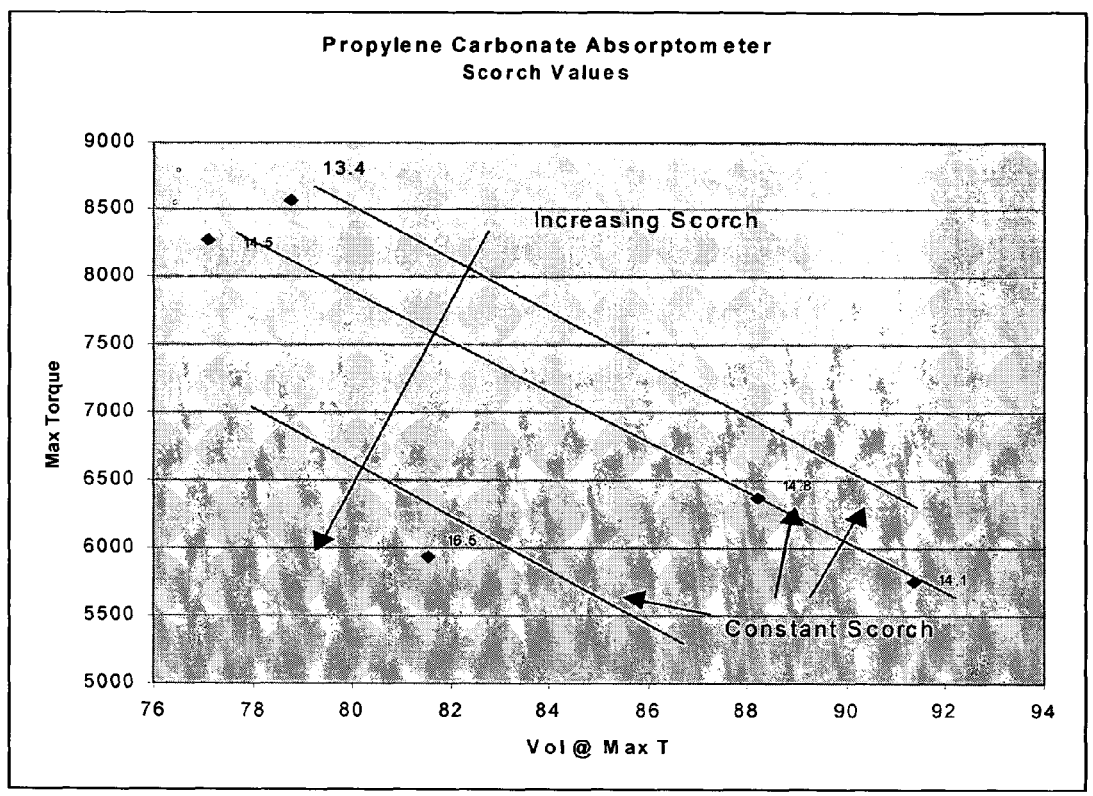

The results show that, while the 5 carbon blacks are very similar based on their morphological values, they are different based on measures of interfacial potential. The data is also shown in FIG. 6 which shows the scorch values versus the maximum torque and volume at maximum torque.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of forming a composition comprising a candidate particulate material and a matrix, wherein the method comprises
providing one or more candidate particulate material selected from carbon black or silica for said matrix;
said candidate particulate material having at least one morphological value of the candidate particulate material selected from the group consisting of shape, size, and structure or having at least one chemical value of the candidate particulate material selected from at least one of the group consisting of overall composition, surface composition, and extractable materials, and
measuring (a) at least one homogenous interaction parameter for at least one candidate particulate material, wherein said homogeneous interaction parameter relates to how the candidate particulate material interacts with itself, and/or (b) at least one heterogeneous interaction parameter for at least one candidate particulate material and the matrix, wherein said heterogeneous interaction parameter relates to how the particulate material and the matrix interact with each other;
adding at least one of said candidate particulate material to said matrix based upon the relationship of:
A) at least one performance property of the composition and
B) 1) said at least one homogeneous interaction parameter for each candidate particulate material, or
B) 2) said at least one homogeneous interaction parameter for each candidate particulate material and at least one heterogeneous interaction parameter for each candidate particulate material and the matrix,
and wherein said candidate particulate material and matrix once combined, form a composition that is within a specified performance property based at least in part on i) said homogenous and/or heterogeneous interaction parameter and ii) said morphological value or chemical value.

2. The method of claim 1, wherein the homogeneous interaction parameter comprises at least one interfacial potential property value, at least one value derived from an interfacial potential property value, at least one component of an interfacial potential property value, or combinations thereof for the particulate material, wherein the particulate material being measured with respect to physical phenomena that responds to interfacial potential property after effects of morphology have been removed.

3. The method of claim 2, wherein the heterogeneous interaction parameter comprises at least one interfacial potential property value, at least one value derived from an interfacial potential property value, at least one component of an interfacial potential property value, or combinations thereof for the particulate material and for the matrix, wherein the particulate material or matrix are measured with respect to physical phenomena that responds to morphology as well as an interfacial potential property of said particulate material or matrix.

4. The method of claim 1, wherein the selected candidate particulate material has an interfacial potential property value, value derived from an interfacial potential property value, component of an interfacial potential property value, or combinations thereof which results in a target value for the performance property of the composition, wherein the target value is at least one measure of phenomena selected from the group consisting of one or more of interfacial potential by masstone, interfacial potential by gas adsorption techniques, interfacial potential from adsorption from solution, interfacial potential from light scattering or disc centrifuge, interfacial potential by oil absorption, interfacial potential by wicking rates, interfacial potential by rheological tests, interfacial potential by sedimentation volumes, interfacial potential by phase segregations, interfacial potential by inverse gas chromatography, interfacial potential by spreading pressure, interfacial potential by drop contact angle, interfacial potential by measuring the pressure of gas to remove a probe liquid from the pores of a packed bed of the particulate material after it has been filled or partly filled by the liquid, interfacial potential by measuring the centrifugal force necessary to immerse particles of the particulate material floating on a probe liquid, interfacial potential by measuring the two-dimensional pressure sufficient to force particles of the particulate material floating on a probe liquid in a Langmuir trough, interfacial potential by measuring the relative adsorption of dye probes, interfacial potential by measuring the heat when the particulate material is immersed into a probe liquid, interfacial potential by measuring the heat released when a test adsorbate is adsorbed by the particulate material, and interfacial potential by measuring the sediment volumes in an homologous series of test liquids.

5. The method of claim 1, further comprising the step of determining the relationship between A) and B): comprising obtaining at least one trend and/or functional relationship between A) at least one performance property of two or more compositions, each of said compositions comprising the matrix and a particulate material, and B) 1) at least one homogeneous interaction parameter for the particulate material or B) 2) at least one homogeneous interaction parameter for the particulate material and at least one heterogeneous interaction parameter for the particulate material and the matrix.

6. The method of claim 1, wherein the particulate material is carbon black.

7. The method of claim 1, wherein the particulate material is fumed silica.

8. The method of claim 1, wherein the matrix comprises at least one polymer, solvent, colorant, surfactant, different particulate material, or combinations thereof.

9. The method of claim 1, wherein the matrix is a polymer.

10. The method of claim 3, wherein the interfacial potential property value, value derived from an interfacial potential property value, component of an interfacial potential property value, or combinations thereof for the particulate material and/or the matrix are determined by a liquid absorptometry method.

11. The method of claim 10, wherein the absorptometry method uses a liquid other than DBP or paraffin oil.

12. The method of claim 11, wherein the absorptometry method uses propylene carbonate, water, ethylene glycol, or mixtures thereof.

13. The method of claim 3, wherein the interfacial potential property value, value derived from an interfacial potential property value, component of an interfacial potential property value, or combinations thereof for the particulate material and/or the matrix are determined by a wicking rate method comprising comparing the wicking rate of two or more different liquids in a particulate packed column.

14. The method of claim 13, wherein the wicking rate method uses nonane, hexadecane, isoalkanes, ethylene glycol, formamide, bromonaphthalene, acetonitrile, benzaldehyde, propylene carbonate, aniline, cyclohexanol, nitroanisole, dichlorobenzene, water, or mixtures thereof.

15. The method of claim 3, wherein the interfacial potential property value, value derived from an interfacial potential property value, component of an interfacial potential property value, or combinations thereof for the particulate material and/or the matrix are determined by a yield point method comprising measuring a degree of flocculation of the particulate material.

16. The method of claim 15, wherein the yield point method uses a hydrocarbon.

17. The method of claim 16, wherein the hydrocarbon is paraffin oil, hexadecane, nonane, or mixtures thereof.

18. The method of claim 3, wherein the interfacial potential property value, value derived from an interfacial potential property value, component of an interfacial potential property value, or combinations thereof for the particulate material and/or the matrix are determined by a interfacial potential vapor adsorption method comprising using an inert gas for gas adsorption analysis.

19. The method of claim 18, wherein the interfacial potential vapor adsorption method uses pentane, nonane, acetonitrile, methylene chloride, water, or mixtures thereof.

20. The method of claim 3, wherein the interfacial potential property value, value derived from an interfacial potential property value, component of an interfacial potential property value, or combinations thereof for the particulate material and/or the matrix are determined by an IGC method comprising measuring retention time of a gas probe flowing through a packed bed of particulate material.

21. The method of claim 20, wherein the IGC method uses butane, pentane, hexane, heptane, tetrahydrofuran, acetone, ethyl acetate, ether, chloroform, acetonitrile, or mixtures thereof.

22. The method of claim 1, wherein the performance property is conductivity, dispersibility, impact strength, color, reinforcement, powder flow, tribocharging, and rheology.

23. The method of claim 1, wherein the relationship is the difference between the work of cohesion for the particulate material and the work of adhesion for the particulate material and the matrix.

24. The method of claim 1, wherein the method further comprises the step of selecting the candidate particulate material based on at least one morphological value of the particulate material selected from the group consisting of shape, size, and structure.

25. The method of claim 1, wherein the method further comprises the step of selecting the candidate particulate material based on at least one chemical value of the particulate material selected from at least one of the group consisting of overall composition, surface composition, and extractable materials.

26. The method of claim 3, further comprising the step of determining the interfacial potential property value, the value derived from an interfacial potential property value, the component of an interfacial potential property value, or combinations thereof for the matrix, wherein the step of determining the interfacial potential property value, the value derived from an interfacial potential property value, the component of an interfacial potential property value, or combinations thereof for the matrix comprises determining the performance property of a composition comprising the matrix and at least one probe particulate material having a predetermined interfacial potential property value, value derived from an interfacial potential property value, component of an interfacial potential property value, or combinations thereof, and wherein the performance property is selected from the group consisting of molecular weight, molar volume, dipole moment, relative permittivity, viscosity, density, surface tension, melting point, glass transition temperature, color, and UV absorption.

27. The method of claim 3, wherein the matrix has a predetermined interfacial potential property value, the value derived from an interfacial potential property value, the component of an interfacial potential property value, or combinations thereof, as derived from one or more of Hildebrand parameters, hydrogen bonding characteristics, electrostatic factors, fractional polarity, Hansen solubility parameters, Snyder's Polarity index, or solvatochromic parameters.

28. The method of claim 3, further comprising the step of determining a surrogate matrix having a predetermined interfacial potential property value, value derived from an interfacial potential property value, component of an interfacial potential property value, or combinations thereof, wherein said surrogate matrix comprises a chemically related formulation of a customer's exact formulation.

29. The method of claim 28, further comprising the step of selecting the candidate particulate material based on a predetermined relationship between:
   A) at least one performance property of a composition comprising the surrogate matrix and the particulate material, and
   B) a combination of
      i) at least one interfacial potential property value, at least one value derived from an interfacial potential property value, at least one component of an interfacial potential property value, or combinations thereof for the particulate material and
      ii) at least one interfacial potential property value, at least one value derived from an interfacial potential property value, at least one component of an interfacial potential property value, or combinations thereof for the surrogate matrix.

30. The method of claim 29, further comprising the step of determining the relationship between A) and B).

31. A method of forming a composition comprising a candidate particulate material and a matrix, said candidate particulate material having at least one morphological value of the candidate particulate material selected from the group consisting of shape, size, and structure or having at least one chemical value of the candidate particulate material selected from at least one of the group consisting of overall composition, surface composition, and extractable materials, and,
   wherein the method comprises providing one or more candidate particulate material selected from carbon black or silica for said matrix and determining a relationship by:
   A) measuring at least one performance property of the composition and
   B) measuring 1) at least one homogeneous interaction parameter for the particulate material, wherein said homogeneous interaction parameter relates to how the particulate material interacts with itself, or
   B) 2) at least one homogeneous interaction parameter for the particulate material and at least one heterogeneous interaction parameter for the particulate material and the matrix, wherein said heterogeneous interaction parameter relates to how the particulate material and the matrix interact with each other,
adding at least one of said candidate particulate material to said matrix based upon the relationship, wherein the selected candidate matrix has an interfacial potential property value, value derived from an interfacial potential property value, component of an interfacial potential property value, or combinations thereof which results in a target value for the performance property of the composition, and wherein said candidate particulate material and matrix once combined, form a composition that is within a specified performance property based at least in part on i) said homogenous and/or heterogeneous interaction parameter and ii) said morphological value or chemical value.

32. The method of claim 31, wherein the homogeneous interaction parameter comprises at least one interfacial potential property value, at least one value derived from an interfacial potential property value, at least one component of an interfacial potential property value, or combinations thereof for the particulate material.

33. The method of claim 32, wherein the heterogeneous interaction parameter comprises at least one interfacial potential property value, at least one value derived from an interfacial potential property value, at least one component of an interfacial potential property value, or combinations thereof for the particulate material and for the matrix.

34. The method of claim 31, further comprising the step of determining the relationship between A) and B).

35. The method of claim 2, wherein the particulate material being measured with respect to physical phenomena that responds both to morphology and interfacial potential property, wherein phenomenon that respond to interfacial potential are assigned an interfacial potential property value to the particulate material where at least one of the following conditions is met selected from the group consisting of:
   A) effect of morphology is eliminated by also measuring the physical phenomena with an inert probe wherein an inert probe is one for which the interfacial potential is negligible;
   B) an external parameter selected from pressure or temperature is changed and the response to that parameter allows an independent calculation of one or more morphological and interfacial potential values; and
   C) the physical phenomenon is measured with the same particulate material in different fluids.

\* \* \* \* \*